US009683263B2

(12) United States Patent
Henderson et al.

(10) Patent No.: US 9,683,263 B2
(45) Date of Patent: Jun. 20, 2017

(54) DETECTION AND TREATMENT OF IRRITABLE BOWEL SYNDROME

(71) Applicant: THE UNITED STATES OF AMERICA, as represented by the secretary, DEPARTMENT OF HEALTH & HUMAN SERVICES, Washington, DC (US)

(72) Inventors: Wendy A. Henderson, Bethesda, MD (US); Ralph M. Peace, Durham, NC (US); Nicolaas H. Fourie, Washington, DC (US); Sarah K. Abey, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/892,999

(22) PCT Filed: May 19, 2014

(86) PCT No.: PCT/US2014/038638
§ 371 (c)(1),
(2) Date: Nov. 20, 2015

(87) PCT Pub. No.: WO2014/189850
PCT Pub. Date: Nov. 27, 2014

(65) Prior Publication Data
US 2016/0153041 A1 Jun. 2, 2016

Related U.S. Application Data

(60) Provisional application No. 61/825,154, filed on May 20, 2013, provisional application No. 61/825,489, filed on May 20, 2013.

(51) Int. Cl.
C12Q 1/68 (2006.01)
A61K 31/70 (2006.01)
A61K 31/7088 (2006.01)
A61K 31/711 (2006.01)
C12N 15/113 (2010.01)
C12N 5/00 (2006.01)

(52) U.S. Cl.
CPC ........ C12Q 1/6883 (2013.01); A61K 31/7088 (2013.01); A61K 31/711 (2013.01); C12N 15/113 (2013.01); C12N 2310/113 (2013.01); C12N 2320/30 (2013.01); C12Q 2600/158 (2013.01); C12Q 2600/178 (2013.01)

(58) Field of Classification Search
None
See application file for complete search history.

(56) References Cited

U.S. PATENT DOCUMENTS

| 2011/0065771 | A1* | 3/2011 | Colgan | A61K 31/47 514/44 A |
| 2011/0117111 | A1* | 5/2011 | Kwon | C12N 15/111 424/172.1 |
| 2012/0172416 | A1 | 7/2012 | Velin et al. | |
| 2013/0225440 | A1* | 8/2013 | Friedman | C12Q 1/6883 506/9 |
| 2014/0199402 | A1* | 7/2014 | Schmidt | C12N 15/113 424/490 |
| 2015/0031567 | A1* | 1/2015 | Getts | C12Q 1/6883 506/9 |

FOREIGN PATENT DOCUMENTS

WO    WO-2012/047631    4/2012

OTHER PUBLICATIONS

Anderson, et al. "Caught in the Akt: regulation of Wnt signaling in the intestine." *Gastroenterology* 139, No. 3 (2010): 718-722.
Baffa, et al. "MicroRNA expression profiling of human metastatic cancers identifies cancer gene targets." *The Journal of Pathology* 219, No. 2 (2009): 214-221.
Chartoumpekis, et al. "Differential expression of microRNAs in adipose tissue after long-term high-fat diet-induced obesity in mice." *PloS One* 7, No. 4 (2012): e34872.
Chen, et al. "The evolution of gene regulation by transcription factors and microRNAs." *Nature Reviews Genetics* 8, No. 2 (2007): 93-103.
Cortez, et al. "MicroRNA identification in plasma and serum: a new tool to diagnose and monitor diseases." *Expert Opinion on Biological Therapy* 9 (2009): 703-711.
Ding, et al. "Gain of miR-151 on chromosome 8q24. 3 facilitates tumour cell migration and spreading through downregulating RhoGDIA." *Nature Cell Biology* 12, No. 4 (2010): 390-399.
Drossman. "The functional gastrointestinal disorders and the Rome III process." *Gastroenterology* 130, No. 5 (2006): 1377-1390.
Fourie, et al. "Elevated circulating miR-150 and miR-342-3p in patients with irritable bowel syndrome." *Experimental and Molecular Pathology* 96, No. 3 (2014): 422-425.
Gheinani, et al. "Deciphering microRNA code in pain and inflammation: lessons from bladder pain syndrome." *Cellular and Molecular Life Sciences* 70, No. 20 (2013): 3773-3789.
Haller, et al. "Localization-and mutation-dependent microRNA (miRNA) expression signatures in gastrointestinal stromal tumours (GISTs), with a cluster of co-expressed miRNAs located at 14q32. 31." *The Journal of Pathology* 220, No. 1 (2010): 71-86.
Henderson, et al. "Inverse relationship of interleukin-6 and mast cells in children with inflammatory and non-inflammatory abdominal pain phenotypes." *World Journal of Gastrointestinal Pathophysiology* 3, No. 6 (2012): 102.

(Continued)

Primary Examiner — Sean McGarry
(74) Attorney, Agent, or Firm — Klarquist Sparkman, LLP

(57) ABSTRACT

Methods are disclosed herein for identifying a subject with irritable bowel syndrome (IBS). Methods are also disclosed for determining if an agent is effective for the treatment or prevention of IBS. Methods of treating a subject with IBS, such as a subject identified using the disclosed methods, are also provided.

24 Claims, 10 Drawing Sheets

(56) References Cited

OTHER PUBLICATIONS

Kapeller, I et al. "First evidence for an association of a functional variant in the microRNA-510 target site of the serotonin receptor-type 3E gene with diarrhea predominant irritable bowel syndrome." *Human Molecular Genetics* 17, No. 19 (2008): 2967-2977.
Kumar, et al. "Cdc42 regulates neutrophil migration via crosstalk between WASp, CD11b, and microtubules." *Blood* 120, No. 17 (2012): 3563-3574.
Li, et al. "Serum microRNA profiles serve as novel biomarkers for HBV infection and diagnosis of HBV-positive hepatocarcinoma." *Cancer Research* 70, No. 23 (2010): 9798-9807.
Lipscombe, et al. "Alternative splicing: functional diversity among voltage-gated calcium channels and behavioral consequences." *Biochimica et Biophysica Acta (BBA)-Biomembranes* 1828, No. 7 (2013): 1522-1529.
Longchamps, et al. "Letter: gender-associated cell-free microRNA profiles in non-alcoholic fatty liver disease." *Alimentary Pharmacology & Therapeutics* 39, No. 9 (2014): 997-998.
Ma, et al. "miR-150 as a potential biomarker associated with prognosis and therapeutic outcome in colorectal cancer." *Gut* (2011): gutjnl-2011.
Nishida, et al. "Microarray analysis of colorectal cancer stromal tissue reveals upregulation of two oncogenic miRNA clusters." *Clinical Cancer Research* 18, No. 11 (2012): 3054-3070.
Orlova, et al. "MicroRNA modulation in complex regional pain syndrome." *Journal of Translational Medicine* 9, No. 1 (2011): 195.
Pekow, et al. "MicroRNAs in inflammatory bowel disease." *Inflammatory Bowel Diseases* 18, No. 1 (2012): 187-193.
Rome. "Are extracellular microRNAs involved in type 2 diabetes and related pathologies?" *Clinical Biochemistry* 46, No. 10 (2013): 937-945.
Starr, et al. "Biochemical analysis of matrix metalloproteinase activation of chemokines CCL15 and CCL23 and increased glycosaminoglycan binding of CCL16."*Journal of Biological Chemistry* 287, No. 8 (2012): 5848-5860.
Valle-Pinero, et al. "Pro-inflammatory chemokine C-C motif ligand 16 (CCL-16) dysregulation in irritable bowel syndrome (IBS): a pilot study." *Neurogastroenterology & Motility* 23, No. 12 (2011): 1092-1097.
Vasilescu, et al. "MicroRNA fingerprints identify miR-150 as a plasma prognostic marker in patients with sepsis." *PloS One* 4, No. 10 (2009): e7405.
Vicario, et al. "Role of microRNA in IBS with increased gut permeability." *Gut* 59, No. 6 (2010): 710-712.
Wu, et al. "MicroRNAs are differentially expressed in ulcerative colitis and alter expression of macrophage inflammatory peptide-2α." *Gastroenterology* 135, No. 5 (2008): 1624-1635 (2008).
Wu, et al. "Peripheral blood microRNAs distinguish active ulcerative colitis and Crohn's disease." *Inflammatory Bowel Diseases* 17, No. 1 (2011): 241-250.
Xiao, et al. "MiR-150 controls B cell differentiation by targeting the transcription factor c-Myb." *Cell* 131, No. 1 (2007): 146-159.
Zernecke, et al. "Delivery of microRNA-126 by apoptotic bodies induces CXCL12-dependent vascular protection." *Science Signaling* 2, No. 100 (2009): ra81-ra81.
Zhang, et al. "Increased colonic motility in a rat model of irritable bowel syndrome is associated with up-regulation of L-type calcium channels in colonic smooth muscle cells." *Neurogastroenterology & Motility* 22, No. 5 (2010): e162-e170.
Zhang, et al. "Secreted monocytic miR-150 enhances targeted endothelial cell migration." *Molecular Cell* 39, No. 1 (2010): 133-144.
Zhou, et al. "MicroRNA-29a regulates intestinal membrane permeability in patients with irritable bowel syndrome." *Gut* 59, No. 6 (2009): 775-784.
Zhou, et al. "miRNA-based therapies for the irritable bowel syndrome." *Expert Opinion on Biological Therapy* 11, No. 8 (2011): 991-995.

\* cited by examiner

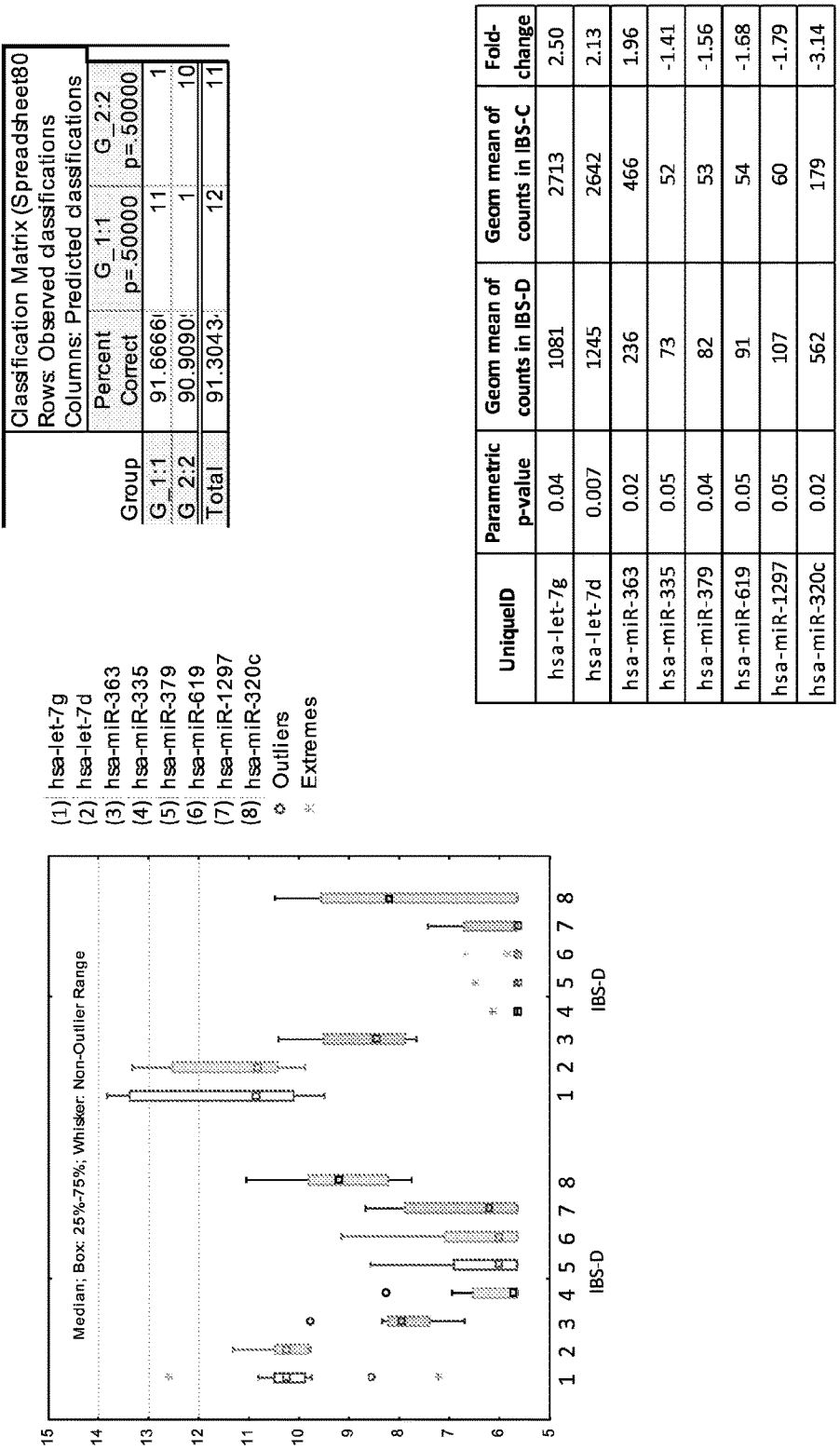

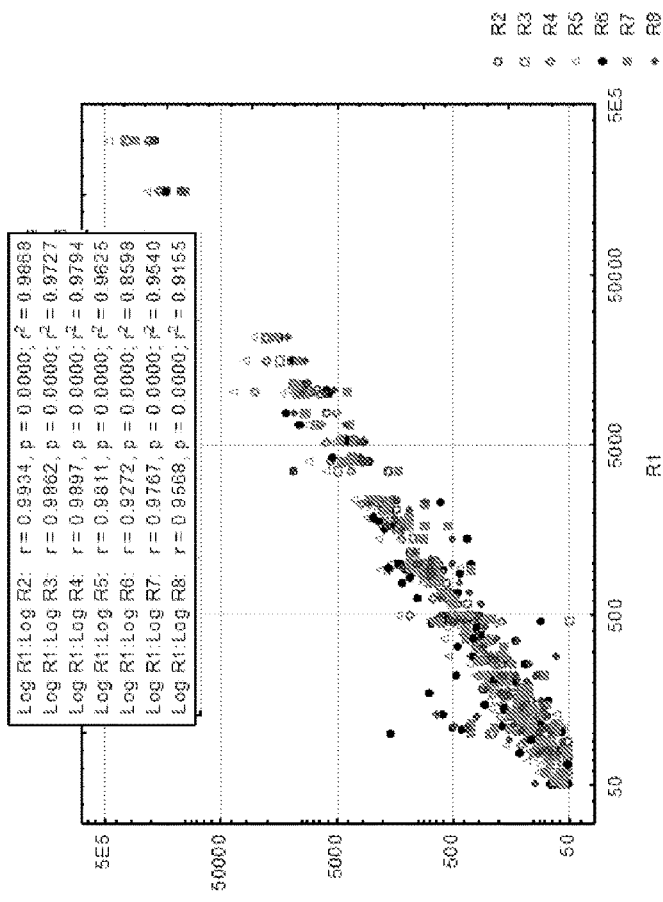
FIG. 10   Validation - Technical Reliability of Data
Low inter-assay variability – technical replicates produce highly consistent counts across batches

DETECTION AND TREATMENT OF IRRITABLE BOWEL SYNDROME

CROSS REFERENCE TO RELATED APPLICATIONS

This is the U.S. National Stage of International Application No. PCT/US2014/038638, filed May 19,2014, which was published in English under PCT Article 21(2), which in turn claims the benefit of U.S. Prov. App. No. 61/825,154, filed on May 20, 2013, and U.S. Prov. App. No. 61/825,489, filed on May 20, 2013. The disclosure of each of the priority applications is incorporated by reference herein in its entirety.

FIELD

This relates to the field of Irritable Bowel Syndrome (IBS), specifically to diagnostic and therapeutic methods for identifying and treating a subject with IBS.

BACKGROUND

IBS is a gastrointestinal disorder characterized by chronic abdominal pain that can negatively impact quality of life and economic productivity. IBS can be classified into multiple subtypes based on the presence of abdominal pain and changes in stool frequency and consistency, including IBS with constipation (IBS-C), IBS with diarrhea (IBS-D), and IBS with alternating constipation and diarrhea (IBS-M). In the United States, IBS is estimated to affect 3 to 20% of the population, with a twice higher prevalence in women.

The standard for diagnosis of IBS has been criticized as unreliable and controversies exist as to the true etiology of the disease. Organic etiologies are rarely found, and IBS is generally diagnosed by excluding other causes for gastrointestinal symptoms. Diagnosis is difficult because of the functional nature of the syndrome and the symptom-based method of diagnosis as well as the similarity in symptoms between IBS and other diseases or disorders. Therefore, there is a need for better diagnostic and therapeutic tools for identifying and treating patients with IBS.

SUMMARY

Provided herein are methods of identifying and treating a subject with IBS. The methods of identifying a subject with IBS can include detection of one or more miRNA expression profiles in the subject, the detection of which identifies the subject as having IBS. Such methods can be superior to known diagnostic methods at least because they do not rely on qualitative assessment of gastrointestinal symptoms.

In some embodiments, a method of identifying a subject with IBS is provided, comprising performing one or more assays that detect an expression level of two or more of miR-150, miR-342-3p, miR-335, miR-151-3p, miR-151-5p, miR-574-3p, and miR-362-5p gene products in a biological sample from the subject. The detected expression level of the gene products is compared to a respective control expression level of the gene products. Detection of an altered expression level of the two or more of the miR-150, miR-342-3p, miR-335, miR-151-3p, miR-151-5p, miR-574-3p, and miR-362-5p gene products as compared to the respective control identifies the subject as a subject with IBS.

In some embodiments, the one or more assays comprise detecting the expression level of the miR-150 and miR-342-3p gene products, and detecting an increased expression level of the miR-150 and miR-342-3p gene products compared to a respective control identifies the subject as a subject with IBS. In some such embodiments the subject is an African American or black human.

In additional embodiments, the one or more assays comprise detecting the expression level of the miR-342-3p, miR-335, miR-151-3p, miR-151-5p, miR-574-3p, and miR-362-5p gene products. Detecting an increased expression level of the miR-335, miR-151-3p, and miR-151-5p gene products, and a decreased expression level of the miR-574-3p, miR-362-5p, and miR-342-3p gene products, as compared to the respective control identifies the subject as a subject with IBS. In some such embodiments, the subject is a Caucasian human.

In additional embodiments, the methods of identifying a subject with IBS comprise performing one or more assays that detect an expression level of hsa-let-7a, hsa-miR-576-5p, hsa-miR-197, hsa-miR-664, and hsa-miR-574-3p gene products in a biological sample from the subject. The detected expression level of the gene products is compared to a respective control expression level of the gene products. Detection of an increase in the expression level of the hsa-let-7a gene product, and a decrease in the expression level of the hsa-miR-576-5p, hsa-miR-197, hsa-miR-664, and hsa-miR-574-3p gene products, as compared to the respective control identifies the subject as a subject with IBS.

In additional embodiments, the method includes identifying a subject with IBS-D, comprising performing one or more assays that detect an expression level of hsa-miR-619, hsa-miR-542-3p, hsa-miR-651, hsa-miR-18a, hsa-miR-335, hsa-miR-137, hsa-miR-320c, hsa-miR-576-5p, hsa-miR-296-5p, Ebv-miR-BHRF1-1, and hsa-miR-197 gene products in a biological sample from the subject. The detected expression level of the gene products is compared to a respective control expression level of the gene products. Detection of an increase in the expression level of the hsa-miR-619, hsa-miR-542-3p, hsa-miR-651, hsa-miR-18a, hsa-miR-335, hsa-miR-137, and hsa-miR-320c gene products, and a decrease in the expression level of the hsa-miR-576-5p, hsa-miR-296-5p, Ebv-miR-BHRF1-1, hsa-miR-197 gene products, as compared to the respective control identifies the subject as a subject with IBS-D.

In additional embodiments, the method includes identifying a subject with IBS-C, comprising performing one or more assays that detect an expression level of hsa-let-7g, hsa-let-7a, hsa-miR-16a, hsa-miR-93, hsa-let-7d, hsa-let-7i, and hsa-miR-98, hsa-miR-548g and hsa-miR-423-3p gene products in a biological sample from the subject. The detected expression level of the gene products to a respective control expression level of the gene products. Detection of an increase in the expression level of the hsa-let-7g, hsa-let-7a, hsa-miR-16a, hsa-miR-93, hsa-let-7d, hsa-let-7i, and hsa-miR-98 gene products, and a decrease in the expression level of the hsa-miR-548g and hsa-miR-423-3p gene products, as compared to the respective control identifies the subject as a subject with IBS-C.

Exemplary biological samples for use with the disclosed methods include blood, tissue, plasma, serum, and stool samples. Exemplary assays to detect an expression level of a gene product can include a polymerase chain reaction, a microarray analysis, or a hybridization reaction assay, such as a reverse transcriptase polymerase chain reaction (RT-PCR) or nanostring assay.

The disclosure also includes methods of treatment that include identifying a subject with IBS, IBS-D, and/or IBC-C as disclosed herein, and administering to the subject a therapeutically effective amount of an agent for the treatment or prevention of IBS, IBS-C, and/or IBS-D.

The foregoing and other features and advantages of this disclosure will become more apparent from the following detailed description of several embodiments which proceeds with reference to the accompanying figures.

BRIEF DESCRIPTION OF THE FIGURES

FIG. 3A shows a heatmap illustrating hsa-miR-335, hsa-miR-574-3p, hsa-miR-342-3p, hsa-miR-151-3p, hsa miR-151-5p, and hsa-miR-362-5p expression in samples from IBS and control subjects. Box and whisker plot of miRNAs that were up-regulated (FIG. 3B) or downregulated (FIG. 3C) in patients with IBS are provided. The small center square represents the mean logged count, the box represents one standard deviation, and the bars represent the range. * p≤0.05, **p≤0.005.

FIGS. 5-10 illustrate altered expression of miRNAs in IBS samples compared to control samples from healthy subjects (FIG. 5), in IBS-D samples compared to health control smaples (FIG. 6), in IBS-C samples compared to healthy control samples (FIG. 7), and in IBS-D samples compared to IBS-C samples (FIGS. 8 and 9) that was obtained using nanostring miRNA expression assays. A classification matrix is shown in each figure, illustrating the percentage of samples that were classified in the correct group based on the miRNA expression patters. The total counts from the nanostring assays, as well as fold change in counts between groups, are shown. FIG. 10 illustrates the low inter-assay variability of the nanostring assays presented herein.

SEQUENCE LISTING

Figure 1A:
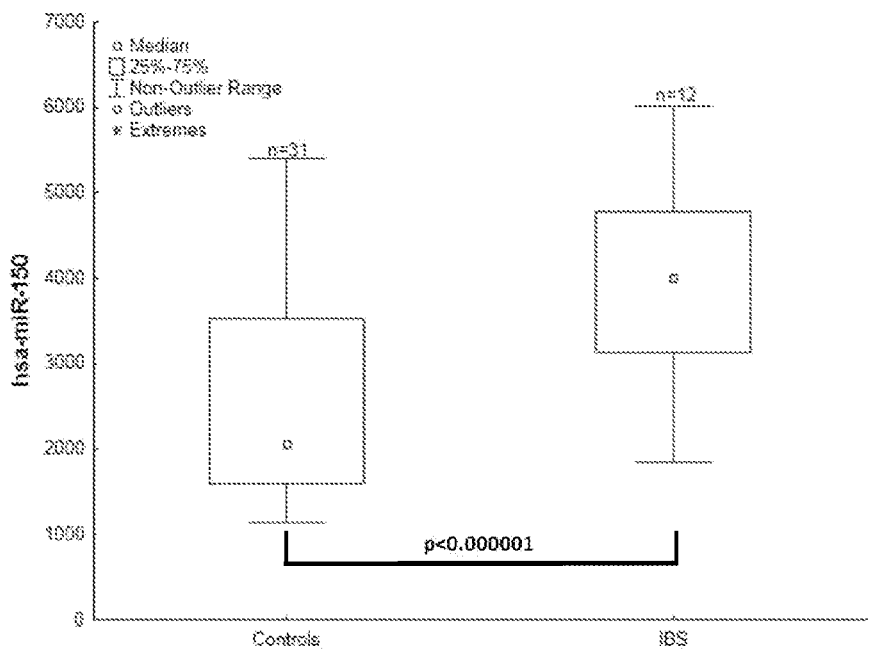
FIGS. 1A and 1B are box and whisker plots showing the differential expression of hsa-miR-150 (FIG. 1A) and hsa-miR-342-3p (FIG. 1B) in samples from healthy subjects or patients with IBS.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~8 kb), which was created on Oct. 27, 2015, which is incorporated by reference herein. In the accompanying sequence listing:

DETAILED DESCRIPTION

Current methods of identifying a subject with IBS are suboptimal. Misdiagnosis leads to delays in treatment and worse outcomes. Better methods of identifying a subject with IBS will reduce risk of misclassification and improve treatment decisions and outcomes. Novel miRNA expression profiles are disclosed herein which can be readily detected by examining circulating RNA in a blood sample (or other samples) from a subject, and can be used to identify a subject with IBS. Detection of the expression profiles is also useful to identify appropriate therapeutic agents for treating IBS in a subject.

I. Terms

Unless otherwise noted, technical terms are used according to conventional usage. Definitions of common terms in molecular biology may be found in Benjamin Lewin, *Genes IX*, published by Jones and Bartlett Publishers, 2007 (ISBN 0763740632); Kendrew et al. (eds.), *The Encyclopedia of Molecular Biology*, published by Blackwell Science Inc., 1998; and Robert A. Meyers (ed.), *Molecular Biology and Biotechnology: a Comprehensive Desk Reference*, published by VCH Publishers, Inc., 1995 (ISBN 1-56081-569-8), and other similar references.

As used herein, the term "comprises" means "includes." Thus, "comprising an agent" means "including an agent" without excluding other elements. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In addition, all GenBank accession numbers and miRBase accession numbers are herein incorporated by reference as they appear in the database on May 22, 2014. In case of conflict, the present specification, including explanations of terms, will control. In order to facilitate review of the various embodiments of the disclosure, the following explanations of specific terms are provided:

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for treating IBS in a subject. Agents include proteins, antibodies, nucleic acid molecules, compounds, small molecules, organic compounds, inorganic compounds, or other molecules of interest. Examples of agents include therapeutic agents, diagnostic agents, and pharmaceutical agents. A therapeutic agent is one that alone or together with an additional compound induces the desired response (such as inducing a therapeutic or prophylactic effect when administered to a subject, including inhibiting or treating IBS). In some examples, a therapeutic agent includes an isolated miRNA gene product that is down-regulated in subjects with IBS or an inhibitor of a miRNA that is up-regulated in subjects with IBS.

Alteration in expression: An alteration in expression of a miRNA gene product refers to a change or difference, such as an increase or decrease, in the level of the miRNA gene product that is detectable in a biological sample relative to a control. An "alteration" in expression includes an increase in expression (up-regulation) or a decrease in expression (down-regulation). In some examples, an alteration in expression includes a change or difference, such as an increase or decrease, in the conversion of the information encoded in a miRNA gene into miRNA gene product. In some examples, the difference is relative to a control or reference value, such as an amount of miRNA expression in a sample from a healthy control subject.

In several embodiments, an alteration in expression of a miRNA gene product can be at least about a 10%, 20%, 30%, 40%, 50%, 60%, 70%, 80%, 90%, 100%, 150%, 200%, or 300% increase or decrease in the level of the miRNA gene product in a sample from a subject compared to a control, a statistical normal, or a standard value chosen for specific study.

Antisense compound: An oligomeric compound that is at least partially complementary to the region of a target nucleic acid molecule (such as a miRNA gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. In some examples, the target nucleic acid molecule is a miRNA gene product (such as those indicated in Table 1).

Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In particular examples herein, the antisense compound is an antisense oligonucleotide, siRNA or ribozyme.

In some examples, an antisense compound is an "antisense oligonucleotide." An antisense oligonucleotide is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

Array: An arrangement of molecules, such as biological macromolecules (such nucleic acid molecules), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least 2, at least 5, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-1000 addressable locations, such as 10-100 addressable locations. In particular examples, an array consists essentially of probes or primers (such as those that permit amplification) specific for the miRNA gene products listed in one or more of Table 1.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

In some examples, the array includes positive controls, negative controls, or both, for example molecules specific for detecting β-actin, 18S RNA, beta-microglobulin, glyceraldehyde-3-phosphate-dehydrogenase (GAPDH), and other housekeeping genes. In one example, the array includes 1 to 20 controls, such as 1 to 10 or 1 to 5 controls.

Biological sample: A biological specimen containing genomic DNA, RNA (including miRNA), protein, or combinations thereof, obtained from a subject. Examples include, but are not limited to, saliva, blood, plasma, serum, urine, tissue, hair, cells, tissue biopsy, surgical specimen, fecal matter, and autopsy material.

Consists of and Consists Essentially of: With regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Control: A "control" refers to a sample or standard used for comparison with a test sample, such as a tissue sample obtained from a healthy subject (or plurality of subjects). In some embodiments, the control is a sample obtained from a healthy subject (or plurality of subjects) (also referred to herein as a "normal" control). In some embodiments, the control is a historical control or standard value (i.e. a previously tested control sample or group of samples that represent baseline or normal values, such as baseline or normal values in a healthy subject). In some examples the control is a standard value representing the average value (or average range of values) obtained from a plurality of patient samples (such as an average value or range of values of miRNA expression for those listed in Table 1, from normal patients).

Downregulated or Decreased: When used in reference to the expression of a nucleic acid molecule (such as a miRNA), refers to any process which results in a decrease in production of a gene product (such as a primary transcript miRNA (pri-miRNA), precursor miRNA (pre-miRNA), or a mature miRNA).

Examples of processes that decrease transcription include those that facilitate degradation of a transcription initiation complex, those that decrease transcription initiation rate, those that decrease transcription elongation rate, those that decrease processivity of transcription and those that increase transcriptional repression.

Gene downregulation can include reduction of expression below an existing level. A downregulation or decrease in the expression of a gene includes any detectable decrease in the production of a gene product, such as a decrease of at least 1.2 fold, at least 1.3 fold, at least 1.4 fold, at least 1.5 fold, at least 2-fold, at least 3-fold, or at least 4-fold, as compared to a control (such an amount of gene expression in a normal cell or sample). In one example, a control is a relative amount of gene expression in a biological sample, such as from a subject that does not have IBS.

Detecting expression of a gene product: Determining the presence of and/or the level of expression of a nucleic acid molecule (such as a miRNA) encoded by a gene in either a qualitative or quantitative manner. Exemplary methods include microarray analysis, nanostring assay, RT-PCR, Northern blot, of specimens from a subject, for example measuring levels of a gene product present in blood, serum, or another biological sample as a measure of expression.

Detecting expression of a miRNA includes detecting expression of either a mature form of the miRNA or a precursor form (i.e., a pri-miRNA or pre-miRNA) that is correlated with expression of the miRNA. Typically, miRNA detection methods involve sequence specific detection, such as by RT-PCR. miRNA-specific primers and probes can be designed using the precursor and mature miRNA nucleic acid sequences that are known in the art. Additionally, various kits are available commercially for detecting miRNA expression levels, such as the nCounter® Human miRNA Expression Assay Kit (available from NanoString Technologies, Seattle, Wash.) and the mirScript PCR system (Qiagen, Valencia, Calif.).

Diagnosis: The process of identifying a disease by its signs, symptoms and results of various tests. The conclusion reached through that process is also called "a diagnosis." Forms of testing commonly performed include blood tests, stool tests, medical imaging, urinalysis, endoscopy and biopsy.

Diagnostically significant amount: An increase or decrease in the expression level of a miRNA gene product in a biological sample that is sufficient to allow one to distinguish one patient population from another, such as a subject with IBS from a subject without IBS. In some embodiments, the diagnostically significant amount is an increase or decrease of at least 1.2 fold (such as at least 1.3-fold at least 1.4-fold, at least 1.5-fold, at least 2-fold, or at least 3-fold) in the expression level of one or more miRNAs relative to a control. A diagnostically significant amount can also be determined by calculating the fold-change in expression of a particular miRNA between two sample types. Microarray analysis is provided herein as one example of how miRNA gene product expression can be detected. However, one of skill in the art will recognize that other methods exist to measure gene expression (such as one of the methods described herein) and variation in detected expression levels can occur depending on the method that is used. Thus, the diagnostically significant amount may vary if another method of detection is used, such as RT-PCR.

Expression: The process by which the coded information of a gene is converted into an operational, non-operational, or structural part of a cell, such as the synthesis of a miRNA. Gene expression can be influenced by external signals. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, gene expression can be monitored to identify a subject with IBS and to detect response to treatment.

The expression of a nucleic acid molecule in a test sample can be altered relative to a control sample, such as a normal sample from a healthy subject. Alterations in expression, such as differential expression, include but are not limited to: (1) overexpression; (2) underexpression; or (3) suppression of expression. Controls or standards for comparison to a sample, for the determination of differential expression, include samples believed to be normal (in that they are not altered for the desired characteristic, for example a sample from a subject who does not have IBS) as well as laboratory values (e.g., range of values), even though possibly arbitrarily set, keeping in mind that such values can vary from laboratory to laboratory. Laboratory standards and values can be set based on a known or determined population value and can be supplied in the format of a graph, figure, or table that permits comparison of measured, experimentally determined values.

Gene expression signature: A gene expression signature includes a distinct or identifiable pattern of levels of gene expression, for instance a pattern of high and low levels of expression of a defined set of genes or gene-indicative nucleic acids such as one or more miRNAs. In some examples, as few as two genes provides a signature, but more genes can be used in a signature, for example, at least three, at least five, at least six, or at least ten. A gene expression signature can be linked to a disease (such as IBS), responsiveness to a therapy, or to any other distinct or identifiable condition that influences gene expression in a predictable way. Gene expression signatures can include relative as well as absolute expression levels of specific genes, and can be viewed in the context of a test sample compared to a baseline or control gene expression signature (such as a sample from the same tissue type from a subject who does not have IBS). In one example, a gene expression signature in a subject is read on an array.

Increase or upregulated: When used in reference to the expression of a nucleic acid molecule (such as a miRNA), refers to any process which results in an increase in production of a gene product (such as a primary transcript miRNA (pri-miRNA), precursor miRNA (pre-miRNA), or a mature miRNA).

Gene upregulation can include increased expression above an existing level. An increase or upregulation in the expression of a gene includes any detectable increase in the production of a gene product, such as an increase of at least 1.2 fold, at least 1.3 fold, at least 1.4 fold, at least 1.5 fold, at least 2-fold, at least 3-fold or at least 4-fold, as compared to a control (such an amount of gene expression in a normal cell or sample). In one example, a control is a relative amount of gene expression in a biological sample, such as from a subject that does not have IBS.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Irritable Bowel Syndrome (IBS): IBS is the most common of all gastrointestinal disorders, estimated to affect 3 to 20% of the population, with a twice higher prevalence in women. Patients with IBS present with disparate symptoms such as, for example, abdominal pain predominantly related to defecation, diarrhea, constipation or alternating diarrhea and constipation, abdominal distention, gas, and excessive mucus in the stool. IBS patients are classified into three groups according to their predominant bowel symptoms: IBS with constipation (IBS-C), IBS with diarrhea (IBS-D) and IBS with alternating symptoms of diarrhea and constipation (IBS-M). Unlike inflammatory bowel disease (IBD), IBS does not involve gross histological inflammation of the small and large intestine, and does not include Crohn's Disease and Ulcerative Colitis. However, some inflammation of parts of the small intestine and colon (which can be chronic or recurrent) can be seen in an IBS patient.

The person of ordinary skill in the art is familiar with standard methods of identifying and treating a subject with IBS. For example, diagnosis of IBS can based on the Rome criteria (I, II, III, or most recent Rome recommended criteria) and according to the symptoms presented by the patients plus the exclusion of other GI disorders. Based on the Rome criteria, IBS can be diagnosed if a patient presents with recurrent abdominal pain or discomfort at least 3 days per month for at least three months, and two or more of (1) the pain or discomfort is reduced upon defecation; (2) the onset of the pain or discomfort is associated with a change in frequency of stool; and (3) the onset of the pain or discomfort is associated with change in form (appearance) of stool.

Level of Expression: An amount, such as of miRNA, that can be measured in a biological sample.

MicroRNA (miRNA or miR): A single-stranded RNA molecule that regulates gene expression in plants, animals and viruses. A gene encoding a miRNA is transcribed to form a primary transcript miRNA (pri-miRNA), which is processed to form a short stem-loop molecule, termed a precursor miRNA (pre-miRNA), followed by endonucleolytic cleavage to form the mature miRNA. Mature miRNAs are approximately 21-23 nucleotides in length and are partially complementary to the 3'UTR of one or more target messenger RNAs (mRNAs). The term "miRNA gene product" includes pri-miRNAs, pre-miRNAs and mature miRNAs (including minor mature miRNA species referred to as miR*). MiRNAs modulate gene expression by promoting cleavage of target mRNAs or by blocking translation of the cellular transcript.

A nomenclature scheme has been well established for miRNAs (Griffiths-Jones et al., Nucleic Acids Res. 34:D140-D144, 2006; Ambros et al., RNA 9:277-279, 2003; Griffiths-Jones, Nucleic Acids Res. 32:D109-D111, 2004). For example, a miRNA name includes a three or four letter species prefix, such as "hsa" for *Homo sapiens*, and a numeric suffix, such as "100," resulting in a complete name of "hsa-miR-100." Mature miRNA sequences expressed from more than one hairpin precursor molecule are distinguished by "-1" and "-2" (such as miR-6-1 and miR-6-2). Related hairpin loci expressing related mature miRNA sequences have lettered suffixes (such as miR-125a and miR-125b). In some cases, mature miRNAs from both the 5' and 3' arms of the hairpin precursor are identified, which are designated "3p" or "5p" (such as miR-151-3p and miR-151-5p). Viral miRNA names relate to the locus from which the miRNA is derived (for example, ebv-miR-BART1 is from the Epstein-Barr virus BART locus).

Most known miRNA sequences are registered and assigned an official number by the miTBase Registry (available online through the University of Manchester at mirbase.org). All miRs referred to by their miRBase registry numbers are herein incorporated by reference as they appear in the miRBase registry as of the filing date of this application.

Subject: Living multi-cellular vertebrate organism, a category that includes human and non-human mammals.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of therapeutic agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, carrier may be sterile, and/or suspended in a unit dosage form containing one or more measured doses of a composition suitable to induce a desired response (such as reduction in the symptoms of IBS). It may also be accompanied by medications for its use for treatment purposes. The unit dosage form may be, for example, in a sealed vial that contains sterile contents or a syringe for injection into a subject.

Polymerase Chain Reaction (PCR): An in vitro amplification technique that increases the number of copies of a nucleic acid molecule (for example, a nucleic acid molecule in a sample or specimen). The product of a PCR can be characterized by standard techniques known in the art, such as electrophoresis, restriction endonuclease cleavage patterns, oligonucleotide hybridization or ligation, and/or nucleic acid sequencing.

In some examples, PCR utilizes primers, for example, DNA oligonucleotides 10-100 nucleotides in length, such as about 15, 20, 25, 30 or 50 nucleotides or more in length (such as primers that can be annealed to a complementary target DNA strand by nucleic acid hybridization to form a hybrid between the primer and the target DNA strand. Primers can be selected that include at least 15, at least 20, at least 25, at least 30, at least 35, at least 40, at least 45, at least 50 or more consecutive nucleotides of a nucleotide sequence of interest. Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990).

Primers: Short nucleic acid molecules, for instance DNA oligonucleotides 10-100 nucleotides in length, such as about 15, 20, 25, 30 or 50 nucleotides or more in length, such as this number of contiguous nucleotides of a nucleotide sequence encoding a protein of interest or other nucleic acid molecule. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length.

In one example, a primer includes at least 15 consecutive nucleotides of a nucleotide molecule, such as at least 18 consecutive nucleotides, at least 20, at least 25, at least 30, at least 35, at least 40, at least 45, at least 50 or more consecutive nucleotides of a nucleotide sequence (such as a gene, miRNA or cDNA). Such primers can be used to amplify a nucleotide sequence of interest, such as the markers listed in Tables A, B, and/or C, for example using PCR.

Probe: A short sequence of nucleotides, such as at least 8, at least 10, at least 15, at least 20, at least 21, at least 25, at least 30, at least 35, at least 40, at least 45, at least 50, at least 55, at least 60, at least 65, at least 70, at least 75, at least 80, at least 85, at least 90, at least 95 or even greater than 100 nucleotides in length, used to detect the presence of a complementary sequence by molecular hybridization. In particular examples, oligonucleotide probes include a label that permits detection of oligonucleotide probe:target sequence hybridization complexes. Such an oligonucleotide probe can also be used on a nucleic acid array, for example to detect a nucleic acid molecule in a biological sample contacted to the array. In some examples, a probe is used to detect the presence of a miRNA listed in Table 1.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, Gene, 73:237-44, 1988; Higgins & Sharp, CABIOS 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity with the genes listed in Table 6 or Table 7 as determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside of the ranges provided.

Small interfering RNA (siRNA): A double-stranded nucleic acid molecule that modulates gene expression through the RNAi pathway (see, for example, Bass, Nature 411:428-9, 2001; Elbashir et al., Nature 411:494-8, 2001; and PCT Publication Nos. WO 00/44895; WO 01/36646; WO 99/32619; WO 00/01846; WO 01/29058; WO 99/07409; and WO 00/44914). siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs," "small interfering RNAs" or "short inhibitory RNAs." As used herein, siRNA molecules need not be limited to those molecules containing only RNA, but further encompasses chemically modified nucleotides and non-nucleotides having RNAi capacity or activity. In an example, a siRNA molecule is one that reduces or inhibits the biological activity or expression of a miRNA gene product.

Treating or Treatment: A therapeutic intervention that reduces a sign or symptom of a disease or pathological condition related to a disease (such as IBS). Treatment can also induce remission or cure of a condition, such as IBS. In particular examples, treatment includes preventing or reducing IBS, for example by inhibiting the full development of IBS in a subject.

Reducing a sign or symptom associated with IBS can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular neoplasm. Prevention of a disease does not require a total absence of IBS. For example, a decrease of at least 30% can be clinically sufficient.

Therapeutically effective amount: An amount of a pharmaceutical preparation that alone, or together with a pharmaceutically acceptable carrier or one or more additional therapeutic agents, induces the desired response, such as reducing or inhibiting one or more signs or symptoms associated with a condition or disease. A therapeutic agent, such as an agent for the treatment or prevention of IBS is administered in therapeutically effective amounts. Effective amounts a therapeutic agent can be determined in many different ways, such as assaying for a reduction in IBS symptoms, change in motility, endoscopic improvement in histology, resolution of abdominal pain symptoms. Effective amounts also can be determined through various in vitro, in vivo or in situ assays.

Therapeutic agents can be administered in a single dose, or in several doses, for example daily, during a course of treatment. However, the effective amount of can be dependent on the source applied, the subject being treated, the severity and type of the condition being treated, and the manner of administration. When administered to a subject, a dosage will generally be used that will achieve target tissue concentrations.

In one example, it is an amount sufficient to partially or completely alleviate symptoms of IBS (such as constipation, diarrhea, or abdominal pain) in a subject. Treatment can involve only slowing the progression of the IBS temporarily, but can also include halting or reversing the progression of the IBS permanently. For example, a pharmaceutical preparation can decrease one or more symptoms of IBS, for example decrease a symptom by at least 20%, at least 30%, at least 40%, at least 50%, at least 70%, at least 90%, at least 98%, or even at least 100%, as compared to an amount in the absence of the pharmaceutical preparation. In some examples, it is an amount of an agent capable of modulating blood levels of one or more of the disclosed miRNAs associated with IBS, by least 20%, at least 30%, at least 40%, at least 50%, at least 60%, at least 70%, at least 80%, at least 90%, at least 95%, at least 98%, or even at least 100% by the agent.

Under conditions sufficient for: A phrase that is used to describe any environment that permits a desired activity.

II. Diagnostic Methods

Methods are provided for identifying a subject with IBS.

In some embodiments, the subject is apparently healthy, such as a subject who does not exhibit symptoms of IBS (for example, does not have chronic abdominal pain or constipation or diarrhea, alternating constipation and diarrhea or does not meet the Rome criteria). In other examples, the subject is suspected of having IBS, such as a subject with chronic abdominal pain. In more examples, the subject is a subjected believed to have IBS, such as a subject determined to have IBS by the Rome criteria (e.g., the Rome III criteria).

In some embodiments, the methods disclosed herein can include evaluating the expression level of one or more of the following:

TABLE 1 miRNA biomarkers for IBS

| miRNA | Sequence | miRBase Accession No. |
|---|---|---|
| ebv-miR-BART6-5p | uaagguugguccaauccauagg (MS; SEQ ID NO: 1) | MIMAT0003414 |
| ebv-miR-BHRF1-1 | uauuaaccugaucagccccgga guugccuguuucaucacuaacc ccgggccugaagagguugacaa (SLS; SEQ ID NO: 2) uaaccugaucagccccggaguu (MS; SRQ ID NO: 3) | MI0001064 |

TABLE 1-continued miRNA biomarkers for IBS

| miRNA | Sequence | miRBase Accession No. |
|---|---|---|
| hsa-let-7a | ugggaugagguaguagguuguauaguuuuagggucacacccaccacuggagauaacuauacaaucuacugucuuuccua (SLS; SEQ ID NO: 4) | MIMAT0000062 |
| hsa-let-7d | ccuaggaagagguaguaggguugcauaguuuuagggcagggauuuugcccacaaggagguaacuauacgaccugcugccuuucuuagg (SLS; SEQ ID NO: 5) | MI0000065 |
| hsa-let-7g | aggcugagguaguaguuuguacaguuugagggucuaugauaccacccgguacaggagauaacugacaggccacugccuugcca (SLS; SEQ ID NO: 6) | MI0000433 |
| hsa-miR-16 | gucagcagugccuuagcagcaguaaauauuggcguuaagauucuaaaauuaucuccaguauuaacugugcugcugaaguaagguugac (SLS; SEQ ID NO: 7) | MI0000070 |
| hsa-miR-18a | uguucuaagguguaucuagugcagauagugaaguagauuagcaucuacugcccuaagugucccuucuggca (SLS: SEQ ID NO: 8) | MI0000072 |
| hsa-miR-18b | uguguuaagguguaucuagugcaguuagugaagcagcuuagaaucuacugcccuaaaugcccuucuggca (SLS; SEQ ID NO: 9) | MI0001518 |
| hsa-miR-93 | cuggggcuccaaagugcuguucgugcagguagugugauuaccaaccuacugcugagcuagcacuucccgagcccccgg (SLS; SEQ ID NO: 10) | MI0000095 |
| hsa-miR-98 | aggauucugcucaugccagggugagguaguaaguuguauuguugugggguagggauauuaggccccaauuagaagauaacuauacaacuuacuacuuucccuggugugugcauauuca (SLS; SEQ ID NO: 11) | MI0000100 |
| hsa-miR-137 | gguccucugacucucuucggugacggguauucuggguggauaaucgauuacguguuauugcuuaagaauacgcuagucgaggagaguaccagcggca (SLS; SEQ ID NO: 12) | MI0000454 |
| hsa-miR-142-3p | uguaguguuuccuacuuuauggau (SEQ ID NO: 13) | MIMAT0000434 |
| hsa-miR-150 | cucccccauggcccugucucccaaccccuuguaccagugcugggcucagacccugguacaggccugggggacagggaccuggggac (SLS; SEQ ID NO: 14) | MI0000479 |
| hsa-miR-151a-3p | cuagacugaagcuccuugagg (MS; SEQ ID NO: 15) | MIMAT0000757 |
| hsa-miR-151a-5p | ucgaggagcucacagucuagu (MS; SHQ ID NO: 16) | MIMAT0004697 |
| hsa-miR-185 | aggggggcgagggauuggagagaaaggcaguuccugauggucccucccccaggggcuggcuuuccucugguccuucccucccca (SLS; SEQ ID NO: 17) | MI0000482 |
| hsa-miR-197 | ggcugugccgggguagagagggcaguggagguaagagcucuucacccuucaccaccuucuccacccagcauggcc (SLS; SEQ ID NO: 18) | MI0000239 |
| hsa-miR-296-5p | agggcccccccucaauccugu (SEQ ID NO: 19) | MIMAT0000690 |
| has-miR-320c | Aaaagcugggguugagagggu (MS; SEQ ID NO: 20) | MIMAT0005793 |
| hsa-miR-335 | uguuugagcgggggucaagagcaauaacgaaaaauguuugucauaaaccguuuuucauuauugcuccugaccuccucucauuugcuauauuca (SLS; SEQ ID NO: 21) | MI0000816 |
| hsa-miR-342-3p | ucucacacagaaaucgcacccgu (MS; SEQ ID NO: 22) | MIMAT0004694 |
| hsa-miR-362-5p | aauccuuggaaccuaggugugagu (MS: SEQ ID NO: 23) | MIMAT0000705 |
| hsa-miR-363 | uguugcggguggaucacgaugcaauuuugaugaguaucauaggagaaaaauugcacgguauccaucuguaaacc (SLS; SEQ ID NO: 24) | MI0000764 |
| hsa-miR-379 | agagaugguagacuauggaacguaggcguuaugauuucugaccuauguaacaugguccacuaacucu (SLS: SEQ ID NO: 25) | MI0000787 |
| hsa-miR-423-3p | agcucggucugagggcccucagu (MS; SEQ ID NO: 26) | MIMAT0001340 |
| hsa-miR-542-3p | ugugacagauugauaacugaaa (MS; SEQ ID NO: 27) | MIMAT0003389 |
| hsa-miR-548g | aguuauuagauuagugcaaaaguaauugcaguuuuugcauuacguucuauggcaaaacuguaauuacuuuuguaccaacauaauacuuc (SLS; SEQ ID NO: 28) | MI0006395 |
| hsa-miR-574-3p | cacgcucaugcacacacccaca (MS: SEQ ID NO: 29) | MIMAT0003239 |
| hsa-miR-576-5p | auucuaauuucuccacgucuuu (MS; SEQ ID NO: 30) | MIMAT0003241 |
| hsa-miR-619 | cgcccaccucagcucccaaaaugcugggauuacaggcaugagccacugcggucgaccaugaccugacauguuugugcccaguacugucaguuugcag (SLS; SEQ ID NO: 31) | MI0003633 |
| hsa-miR-650 | cagugcuggggucucaggagcagcgcucucaggacgucaccaccauggccugggcucugcucuccucacccuccucacucagggacaggugau (SLS; SEQ ID NO: 32) | MI0003665 |

TABLE 1-continued miRNA biomarkers for IBS

| miRNA | Sequence | miRBase Accession No. |
|---|---|---|
| hsa-miR-651 | aaucuaucacugcuuuuuagga uaagcuugacuuuuguucaaau aaaaaugcaaaaggaaagugua uccuaaaaggcaaugacaguuu aauguguuu (SLS; SEQ ID NO: 33) | MI0003666 |
| hsa-miR-664a | gaacauugaaacuggcuaggga aaaugauuggauagaaacuauu auucuauucauuuauccccagc cuacaaaaugaaaaaa (SLS: SEQ ID NO: 34) | MI0006442 |
| hsa-miR-769-5p | ugagaccucugggvucugagcu (MS; SEQ ID NO: 35) | MIMAT0003886 |
| hsa-miR-890 | ggaagugcccuacuuggaaagg caucaguugcuuagauuacaug uaacuauuccccuuucugaguag aguaagucuua (SLS; SEQ ID NO: 36) | MI0005533 |
| hsa-miR-934 | agaaauaaggcuucugucuacu acuggagacacugguaguauaa aacccagagucuccaguaaugg acgggagccuuauuucu (SLS; SEQ ID NO: 37) | MI0005756 |
| hsa-miR-1252 | agaaagaaggaaauugaauuca uuuagaaaagagaauuccaaau gagcuuaauuuccuuuuuucu (SLS; SEQ ID NO: 38) | MI0006434 |
| hsa-miR-1297 | uguuuaucucuagggvugaucu auuagaauuacuuaucugagcc aaaguaauucaaguaauucagg uguagugaaac (SLS; SEQ ID NO: 39) | MI0006358 | miRNAs are produced as a stem loop sequence which is then cleaved to form mature miRNAs
In Table 1, "SLS" refers to Stem Loop Sequence, and "MS" refers to mature sequence.

Biomarkers for identifying a subject with IBS are disclosed in Table 1. In some embodiments, a combination of the biomarkers forms an expression signature that can be used to identify a subject with IBS. For example, in some embodiments, the expression level of at least 2 (such as at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39) of the miRNAs listed in Table 1 forms a signature that can be used to identify a subject with IBS.

For example, in some embodiments, a subject with IBS can be identified by performing one or more assays that detect an alteration in the expression level of ebv-miR-BART6-5p, ebv-miR-BHRF1-1, hsa-let-7a, hsa-let-7d, hsa-let-7g, hsa-miR-16, hsa-miR-18a, hsa-miR-18b, hsa-miR-93, hsa-miR-98, hsa-miR-137, hsa-miR-142-3p, hsa-miR-150, hsa-miR-151a-3p, hsa-miR-151a-5p, hsa-miR-185, hsa-miR-197, hsa-miR-296-5p, hsa-miR-320c, hsa-miR-335, hsa-miR-342-3p, hsa-miR-362-5p, hsa-miR-363, hsa-miR-379, hsa-miR-423-3p, hsa-miR-542-3p, hsa-miR-548g, hsa-miR-574-3p, hsa-miR-576-5p, hsa-miR-619, hsa-miR-650, hsa-miR-651, hsa-miR-664a, hsa-miR-769-5p, hsa-miR-890, hsa-miR-934, hsa-miR-1252, and hsa-miR-1297 gene products in a biological sample from the subject compared to a control.

In some embodiments, a subject with IBS can be identified by performing one or more assays that detect an alteration in the expression level of hsa-miR-150 and hsa-miR-342-3p gene products in a biological sample from the subject (such as a blood sample) compared to a respective control expression level of those gene products. In some embodiments, a subject with IBS can be identified by performing one or more assays that detect an increase in the expression level of hsa-miR-150 and hsa-miR-342-3p gene products in a biological sample from the subject (such as a blood sample) compared to a control. In some embodiments the detected increase in the expression level of hsa-miR-150 and hsa-miR342-3p gene products is at least a 1.5-fold increase in expression compared to the control. In some such embodiments, the subject is an African American or black subject, for example, the subject can be a subject that self-identifies as an African American or black subject.

In some embodiments, a subject with IBS can be identified by performing one or more assays that detect an alteration in the expression level of two or more of hsa-miR-335, hsa-miR-151-5p, hsa-miR-151-3p, hsa-miR-574-3p, hsa-miR-362-5p, hsa-miR-342-3p gene products in a biological sample from the subject (such as a blood sample) compared to a respective control expression level of those gene products. In some embodiments, a subject with IBS can be identified by performing one or more assays that detect an increase in the expression level of hsa-miR-335, hsa-miR-151-5p, and hsa-miR-151-3p gene products, and a decrease in the expression level of hsa-miR-574-3p, hsa-miR-362-5p, hsa-miR-342-3p gene products in a biological sample from the subject (such as a blood sample) compared to a control. In some embodiments the detected increase in the expression level of hsa-miR-335, hsa-miR-151-5p, and hsa-miR-151-3p gene products is at least a 1.5-fold increase in expression compared to the control, and/or the detected decrease in the expression level of hsa-miR-574-3p, hsa-miR-362-5p, hsa-miR-342-3p gene products is at least a 1.5-fold decrease in expression compared to the control. In some such embodiments, the subject is a Caucasian subject, for example, the subject can be a subject that self-identifies as a Caucasian subject.

In some embodiments, a subject with IBS can be identified by performing one or more assays that detect an increase in the expression level of hsa-let-7a gene product, and a decrease in the expression level of hsa-miR-576-5p, hsa-miR-197, hsa-miR-664, and hsa-miR-574-3p gene products in a biological sample from the subject (such as a blood sample) compared to a respective control expression level of those gene products. In some embodiments the detected increase in the expression level of hsa-let-7a gene products is at least a 1.2-fold increase in expression compared to the control, and/or the detected decrease in the expression level of hsa-miR-576-5p, hsa-miR-197, hsa-miR-664, and hsa-miR-574-3p gene products is at least a 1.2-fold decrease in expression compared to the control. In one embodiment, the detected increase in the expression level of hsa-let-7a gene products can be at least a 1.4-fold increase in expression compared to the control, and/or the detected decrease in the expression level of hsa-miR-576-5p, hsa-miR-197, hsa-miR-664, and hsa-miR-574-3p gene products is at least a 1.2-, 1.4-, 1.2-, and 1.2-fold decrease in expression compared to the control, respectively.

In some embodiments, a subject with IBS-D can be identified by performing one or more assays that detect an increase in the expression level of hsa-miR-619, hsa-miR-542-3p, hsa-miR-651, hsa-miR-18a, hsa-miR-335, hsa-miR-137, and hsa-miR-320c gene products, and a decrease in the expression level of hsa-miR-576-5p, hsa-miR-296-5p, EbvmiR-BHRF1-1, hsa-miR-197 gene products in a biological sample from the subject (such as a blood sample) compared to a respective control expression level of those gene products. In some embodiments the detected increase in the expression level of hsa-miR-619, hsa-miR-542-3p, hsa-miR-651, hsa-miR-18a, hsa-miR-335, hsa-miR-137, and hsa-miR-320c gene products is at least a 1.2-fold increase in expression compared to the control, and/or the detected decrease in the expression level of hsa-miR-576-5p, hsa-miR-296-5p, Ebv-miR-BHRF1-1, hsa-miR-197 gene products is at least a 1.2-fold decrease in expression compared to the control. In one embodiment, the detected increase in the expression level of hsa-miR-619, hsa-miR-542-3p, hsa-miR-651, hsa-miR-18a, hsa-miR-335, hsa-miR-137, and hsa-miR-320c gene products can be at least a 1.5-, 1.4, 1.3, 1.3, 1.2, 1.2, and 2.5-fold increase in expression compared to the control, respectively, and/or the detected decrease in the expression level of hsa-miR-576-5p, hsa-miR-296-5p, Ebv-miR-BHRF1-1, hsa-miR-197 gene products is at least a 1.2-, 1.4-, 1.5-, and 1.6-fold decrease in expression compared to the control, respectively.

In some embodiments, a subject with IBS-C can be identified by performing one or more assays that detect an increase in the expression level of hsa-let-7g, hsa-let-7a, hsa-miR-16a, hsa-miR-93, hsa-let-7d, hsa-let-7i, and hsa-miR-98 gene products, and a decrease in the expression level of hsa-miR-548g and hsa-miR-423-3p gene products in a biological sample from the subject (such as a blood sample) compared to a respective control expression level of those gene products. In some embodiments the detected increase in the expression level of hsa-let-7g, hsa-let-7a, hsa-miR-16a, hsa-miR-93, hsa-let-7d, hsa-let-7i, and hsa-miR-98 gene products is at least a 1.2-fold increase in expression compared to the control, and/or the detected decrease in the expression level of hsa-miR-548g and hsa-miR-423-3p gene products is at least a 1.2-fold decrease in expression compared to the control. In one embodiment, the detected increase in the expression level of hsa-let-7g, hsa-let-7a, hsa-miR-16a, hsa-miR-93, hsa-let-7d, hsa-let-7i, and hsa-miR-98 gene products can be at least a 2-, 2, 1.8, 1.5, 1.5, 1.5, and 1.2-fold increase in expression compared to the control, respectively, and/or the detected decrease in the expression level of hsa-miR-548g and hsa-miR-423-3p gene products is at least a 1.4- and 1.4-fold decrease in expression compared to the control, respectively.

In some embodiments, a subject with IBS-D can be distinguished from a subject with IBS-C by performing one or more assays that detect an increase in the expression level of hsa-miR-342-3p, hsa-miR-185, and hsa-miR-150 gene products, and a decrease in the expression level of hsa-miR-934 and hsa-miR-548g gene products in a biological sample from the subject (such as a blood sample) compared to a respective control expression level of those gene products. In some embodiments the detected increase in the expression level of hsa-miR-342-3p, hsa-miR-185, and hsa-miR-150 gene products is at least a 1.1-fold increase in expression compared to the control, and/or the detected decrease in the expression level of hsa-miR-934 and hsa-miR-548g gene products is at least a 1.1-fold decrease in expression compared to the control. In one embodiment, the detected increase in the expression level of hsa-miR-342-3p, hsa-miR-185, and hsa-miR-150 gene products can be at least a 1.1-fold increase in expression compared to the control, respectively, and/or the detected decrease in the expression level of hsa-miR-934 and hsa-miR-548g gene products is at least a 1.3- and 1.5-fold decrease in expression compared to the control, respectively.

In some embodiments, a subject with IBS-D can be distinguished from a subject with IBS-C by performing one or more assays that detect an increase in the expression level of hsa-let-7g, hsa-let-7d, and hsa-miR-363 gene products, and a decrease in the expression level of hsa-miR-335, hsa-miR-379, hsa-miR-619, hsa-miR-1297, and hsa-miR-320c gene products in a biological sample from the subject (such as a blood sample) compared to a respective control expression level of those gene products. In some embodiments the detected increase in the expression level of hsa-let-7g, hsa-let-7d, and hsa-miR-363 gene products is at least a 1.4-fold increase in expression compared to the control, and/or the detected decrease in the expression level of hsa-miR-335, hsa-miR-379, hsa-miR-619, hsa-miR-1297, and hsa-miR-320c gene products is at least a 1.4-fold decrease in expression compared to the control. In one embodiment, the detected increase in the expression level of hsa-let-7g, hsa-let-7d, and hsa-miR-363 gene products can be at least a 2-fold increase in expression compared to the control, respectively, and/or the detected decrease in the expression level of hsa-miR-335, hsa-miR-379, hsa-miR-619, hsa-miR-1297, and hsa-miR-320c gene products is at least a 1.4-, 1.5, 1.6, 1.7, and 3.0-fold decrease in expression compared to the control, respectively.

Any of the above embodiments of identifying a subject with IBS, IBS-D, or IBS-C can further include detecting a decrease in the expression level of ebv-miR-BHRF1-1 and/or ebv-miR-BART6-5p gene products in a sample from the subject as compared to a control.

The expression of the miRNAs listed in Table 1, or in any of the expression profiles listed above, also can be used to assess the efficacy of a therapeutic protocol for the treatment or prevention of IBS. In some embodiments, methods are provided for evaluating the efficacy of a treatment protocol that includes any therapy for IBS designed to reverse or slow the progression of IBS, including but not limited to treatment with pharmaceutical agents know to be useful for treating IBS, such as those listed below. In these embodiments, a sample can be taken from a subject prior to initiation of therapy. After therapy is initiated, an additional sample is taken from the subject. A decrease (or increase) in the expression level of miRNAs that are upregulated (or downregulated) in IBS indicates that the therapy is efficacious. In addition, the subject can be monitored over time to evaluate the continued effectiveness of the therapeutic protocol. The effect of different dosages can also be evaluated, by comparing the expression of markers in a sample from the subject receiving a first dose to the expression of the same markers in a sample from the subject receiving a second (different) dose. The methods can be repeated 1, 2, 3, 4, 5, 6, 7, 8, 9, 10 or more times to determine the lowest dose of a pharmaceutical agent that is effective for treating the subject, and/or the shortest duration of administration that is effective for treating the subject. Thus, the methods can be used over the course of a therapeutic regimen to monitor the efficacy of a pharmaceutical agent for the treatment of the subject.

In some embodiments, a subject identified as having IBS is then treated for IBS, for example as discussed below. In additional embodiments, a subject that is suspected of having, or at risk of having, IBS is selected for the diagnostic methods. For example, a subject exhibiting any of the symptoms of IBS (e.g., chronic abdominal pain and constipation or diarrhea) can be selected for the diagnostic methods.

An explanation of exemplary methods of detecting miRNA expression in a sample, and samples for use in such methods, follows:

A. Detecting miRNA Expression

The expression of the one or more miRNA gene products associated with IBS can be detected using any one of a number of methods well known in the art. In some examples, the expression level of the miRNA is quantified. Detection and quantification of miRNA expression can be achieved by any one of a number of methods well known in the art including those described herein. U.S. Patent Application Publication Nos. 2006/0211000 and 2007/0299030 describe methods of miRNA detection and quantification. Further, general methods for miRNA extraction are well known in the art and several commercially available kits are available for such purposes (e.g., nCounter® Human miRNA Expression Assay Kit (available from NanoString Technologies, Seattle, Wash.; mirVana® miRNA detection kit from Life Technologies, Carlsbad, Calif.). Using the known sequences for a miRNA of interest, specific probes and primers can be designed for use in the detection methods described herein as appropriate.

The sequences of precursor miRNAs and mature miRNAs are publicly available, such as through the miRBase database, available online by the University of Manchester, and formerly maintained by the Sanger Institute (see Griffiths-Jones et al., *Nucleic Acids Res.* 36:D154-D158, 2008; Griffiths-Jones et al., *Nucleic Acids Res.* 34:D140-D144, 2006; and Griffiths-Jones, *Nucleic Acids Res.* 32:D109-D111, 2004).

In some cases, the miRNA detection method requires isolation of nucleic acid from a sample, such as a cell, biological fluid sample or tissue sample (for example, blood sample). Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs. An example of a commercially available tool for total RNA extraction from blood samples is the PAXGene Blood miRNA extraction kit (PreAnalytiX, Qiagen, Valencia, Calif., USA).

Any one of a number of methods for detecting expression of a gene of interest (including miRNAs) known in the art can be used to detect expression of a miRNA, including methods based on hybridization analysis of polynucleotides. A number of these methods, including qRT-PCR, nanostring, array, microarray, in situ hybridization, in situ PCR, SAGE are described in further detail below. miRNA detection can also be accomplished by deep sequencing, according to methods known in the art (Creighton et al., *Brief Bioinform.* 10(5):490-2009 Ma497, 2009). The results of gene expression analysis can be transmitted using any one of a number of output devices or formats known in the art. For example, the output device can be a visual output device, such as a computer screen or a printed piece of paper. In other examples, the output device can be an auditory output device, such as a speaker. In other examples, the output device is a printer. In some cases, the data is recorded in a patient's electronic medical record.

Nanostring. In some embodiments, miRNAs can be detected without amplification using nanostring expression analysis, for example, using the nCounter Analysis System (commercially available from NanoString Technologies, Seattle, Wash.). The basis of the nCounter® Analysis system is the unique code assigned to each gene to be assayed (International Patent Application No. PCT/US2008/059959 and Geiss et al. *Nature Biotechnology.* 2008. 26(3): 317-325; the contents of which are each incorporated herein by reference in their entireties). The code is composed of an ordered series of colored fluorescent spots which create a unique barcode for each target to be assayed. A pair of probes is designed for each target (such as the miRNAs listed in Table 1), a biotinylated capture probe and a reporter probe carrying the fluorescent barcode. After hybridization, excess probes are removed, and probe/target complexes are analyzed in accordance with the manufacturer's protocol. The expression level of a target is measured by imaging each sample and counting the number of times the code for that target is detected. Additional information concerning the use of nanostring assays to detect expression levels of miRNAs is provided in the Examples.

Arrays. In some embodiments, arrays can be used to evaluate miRNA expression, for example to identify a subject with IBS. When describing an array that comprises probes or primers specific for a particular set of miRNAs, such an array includes probes or primers specific for the recited miRNAs (such as those provided in Table 1), and can further include control probes (for example to confirm the incubation conditions are sufficient). In one example, an array is a multi-well plate (e.g., 98 or 364 well plate).

In one example, the array includes, consists essentially of, or consists of probes or primers that can recognize the miRNAs listed in Table 1 and optionally one or more control probes. The oligonucleotide probes or primers can further include one or more detectable labels, to permit detection of hybridization signals between the probe and target sequence (such as one of the miRNAs disclosed herein).

Microarray analysis of miRNAs can be accomplished according to any method known in the art (see, for example, PCT Publication No. WO 2008/054828; Ye et al., *Nat. Med.* 9(4):416-423, 2003; Calin et al., *N. Engl. J. Med.* 353(17): 1793-1801, 2005). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing miRNA extracted from a biological sample, such as a blood sample, is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described herein.

RT-PCR. Methods for quantitating RNA, including miRNA, are well known in the art. In some embodiments, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). However, any suitable reverse transcriptase known in the art can be used for RT-PCR. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA), following the manufacturer's instructions. The derived cDNA can then be used as a template in the subsequent PCR reaction.

Although the PCR step can use a variety of thermostable DNA-dependent DNA polymerases, it often employs the Taq DNA polymerase, which has a 5'-3' nuclease activity but lacks a 3'-5' proofreading endonuclease activity. TaqMan® PCR typically utilizes the 5'-nuclease activity of Taq or Tth DNA polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are miRNAs for the housekeeping genes glyceraldehyde-3-phosphate-dehydrogenase (GAPDH), beta-actin, and 18S ribosomal RNA.

The steps of a representative protocol for quantitating gene expression using fixed, paraffin-embedded tissues as the RNA source, including RNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 µm thick sections of paraffin-embedded tissue samples. The RNA is then extracted, and protein and DNA are removed. Alternatively, RNA is located directly from a tissue, cell or fluid sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as a miRNA. Primers that can be used to amplify a particular miRNA are commercially available (in some instance) or can be designed and synthesized according to well-known methods using publically available sequences of the miRNA.

Serial Analysis of Gene Expression (SAGE). SAGE is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

In Situ Hybridization (ISH). ISH is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of miRNAs. An example of miRNA detection methods in tissues is provided by ISH in which miRCURY LNA™ microRNA Detection Probes is used (Exiqon).

Sample cells or tissues are treated to increase their permeability to allow a probe, such as miRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a adrenal cortex tissue sample. Since the sequences of the miRNAs of interest are known, probes can be designed accordingly such that the probes specifically bind the gene of interest.

In Situ PCR. In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences. Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

B. Biological Samples miRNA can be isolated from a biological sample obtained from the subject, including, but not limited to, mammals such as bovine, avian, canine, equine, feline, ovine, porcine, or primate animals (including humans and non-human primates). Examples of such animals include but are not limited to: carnivores such as cats and dogs; swine including pigs, hogs and wild boars; ruminants or ungulates such as cattle, oxen, sheep, giraffes, deer, goats, bison, camels or horses.

The biological sample obtained from the subject may be any appropriate sample. For example, the biological sample can be peripheral blood, serum, plasma, urine, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool, stool water, pancreatic juice, lavage fluids from sinus cavities, bronchopulmonary aspirates or other lavage fluids. In several embodiments, the sample is a blood, serum, or plasma sample, and the miRNA expression level is determined based on miRNA gene products detected in the blood, serum, or plasma sample. The biological sample may also be a tissue sample or biopsy, from which miRNA can be obtained.

The biological sample may be obtained through a third party, such as a party not performing the analysis of the miRNA. For example, the sample may be obtained through a clinician, physician, or other health care manager of a subject from which the sample is derived. In some embodiments, the biological sample is obtained by the same party analyzing the miRNA.

The volume of the biological sample used for analyzing miRNA can be in the range of between 0.1-20 mL, such as less than about 20, 15, 10, 9, 8, 7, 6, 5, 4, 3, 2, 1 or 0.1 mL. In some embodiments, the sample is about 0.1, 0.2, 0.3, 0.4, 0.5, 0.6, 0.7, 0.8, 0.9, 1.0, 1.5, 2, 3, 4, 5, 6, 7, 8, 9, 10, 11, 12, 13, 14, 15, 16, 17, 18, 19, or 20 mL. In some embodiments, the sample is about 1,000, 900, 800, 700, 600, 500, 400, 300, 250, 200, 150, 100, 75, 50, 25 or 10 µl. For example, a small volume sample could be obtained by a prick or swab.

III. Therapeutic Methods

Also provided herein are methods of treating a subject with IBS. The methods can include identifying a subject with IBS using the diagnostic methods disclosed herein, and then treating the subject with one or more agents for the treatment or prevention of IBS that are known in the art. Additionally, it is disclosed herein that certain miRNAs are differentially expressed in subjects with IBS. As such, an increase in the level of one or more miRNAs down-regulated in subjects with IBS, and/or a decrease in the level of one or more miRNAs up-regulated in subjects with IBS, can be beneficial for inhibiting the development or progression of the IBS and/or for alleviating one or more signs or symptoms of the IBS. Accordingly, the therapeutic methods also can include treating a subject with IBS by administering to the subject a therapeutically effective amount of one or more agents that decrease expression of a miRNA gene product that is up-regulated in IBS, and/or one or more agents that increase the level of a miRNA gene product that is down-regulated in IBS. The agent can be any compound, such as a nucleic acid molecule, polypeptide, small molecule or other compound that is capable of increasing (or decreasing) the expression level or amount of the targeted miRNA gene products.

In embodiments where the agent is administered to decrease the expression or level of a target miRNA, exemplary agents include an antisense compound specific for the miRNA gene product, for example, an antisense oligonucleotide, siRNA or ribozyme, is administered to the subject. In embodiments where the agent is administered to increase the expression or level of a target miRNA, exemplary agents include the isolated miRNA gene product and vectors encoding the miRNA gene product (e.g., encapsulated in a liposome for delivery), such as a plasmid vector or a viral vector. Additional detail concerning therapeutic agents for use in the disclosed methods is provided below.

In some embodiments, a subject with IBS can be treated by administering a therapeutically effective amount of one or more agents that decrease the expression level of hsa-miR-150 and hsa-miR-342-3p gene products in the subject. In some embodiments, a subject is selected for such treatment by first identifying (or confirming) that the subject is a subject with IBS by detecting an increased level of expression of the hsa-miR-150 and hsa-miR342-3p gene products compared to a control, as discussed above. The subject can then be selected for, and/or administered, the treatment for the IBS.

In additional embodiments, a subject with IBS can be treated by administering a therapeutically effective amount of one or more agents that decrease the expression level of hsa-miR-335, hsa-miR-151-5p, and hsa-miR-151-3p gene products, and increase the expression level of hsa-miR-574-3p, hsa-miR-362-5p, hsa-miR-342-3p gene products in the subject. In some embodiments, a subject is selected for the treatment by first identifying (or confirming) that the subject is a subject with IBS by detecting an increase in the expression level of hsa-miR-335, hsa-miR-151-5p, and hsa-miR-151-3p, and a decrease in the expression level of hsa-miR-574-3p, hsa-miR-362-5p, hsa-miR-342-3p, gene products compared to a control, as discussed above. The subject can then be selected for, and/or administered, the treatment for the IBS.

In additional embodiments, a subject with IBS can be treated by administering a therapeutically effective amount of one or more agents that decrease the expression level of hsa-let-7a gene products, and increase the expression level of hsa-miR-576-5p, hsa-miR-197, hsa-miR-664, and hsa-miR-574-3p gene products in the subject. In some embodiments, a subject is selected for the treatment by first identifying (or confirming) that the subject is a subject with IBS by detecting an increase in the expression level of hsa-let-7a, and a decrease in the expression level of hsa-miR-576-5p, hsa-miR-197, hsa-miR-664, and hsa-miR-574-3p, gene products compared to a control, as discussed above. The subject can then be selected for, and/or administered, the treatment for the IBS.

In additional embodiments, a subject with IBS-D can be treated by administering a therapeutically effective amount of one or more agents that decrease the expression level of hsa-miR-619, hsa-miR-542-3p, hsa-miR-651, hsa-miR-18a, hsa-miR-335, hsa-miR-137, and hsa-miR-320c gene products, and increase the expression level of hsa-miR-576-5p, hsa-miR-296-5p, Ebv-miR-BHRF1-1, hsa-miR-197 gene products in the subject. In some embodiments, a subject is selected for the treatment by first identifying (or confirming) that the subject is a subject with IBS-D by detecting an increase in the expression level of hsa-miR-619, hsa-miR-542-3p, hsa-miR-651, hsa-miR-18a, hsa-miR-335, hsa-miR-137, and hsa-miR-320c, and a decrease in the expression level of hsa-miR-576-5p, hsa-miR-296-5p, Ebv-miR-BHRF1-1, hsa-miR-197, gene products compared to a control, as discussed above. The subject can then be selected for, and/or administered, the treatment for the IBS.

In additional embodiments, a subject with IBS-C can be treated by administering a therapeutically effective amount of one or more agents that decrease the expression level of hsa-let-7g, hsa-let-7a, hsa-miR-16a, hsa-miR-93, hsa-let-7d, hsa-let-7i, and hsa-miR-98 gene products, and increase the expression level of hsa-miR-548g and hsa-miR-423-3p gene products in the subject. In some embodiments, a subject is selected for the treatment by first identifying (or confirming) that the subject is a subject with IBS-D by detecting an increase in the expression level of hsa-let-7g, hsa-let-7a, hsa-miR-16a, hsa-miR-93, hsa-let-7d, hsa-let-7i, and hsa-miR-98, and a decrease in the expression level of hsa-miR-548g and hsa-miR-423-3p, gene products compared to a control, as discussed above. The subject can then be selected for, and/or administered, the treatment for the IBS.

A. Agents that Decrease Up-Regulated miRNAs

Provided herein is a method of treating a patient with IBS by administering to the patient a therapeutically effective amount of an agent that inhibits expression of a miRNA gene product that is up-regulated in patients with IBS compared with a control.

As used herein, "inhibiting expression of miRNA gene product" means that the production of the precursor and/or active, mature form of the miRNA gene product after treatment is less than the amount produced prior to treatment. One skilled in the art can readily determine whether miRNA expression has been inhibited in a subject, using the techniques known in the art and described herein Inhibition can occur at the level of gene expression (i.e., by inhibiting transcription of a miRNA gene encoding the miRNA gene product) or at the level of processing (e.g., by inhibiting processing of a miRNA precursor into a mature miRNA).

A therapeutically effective amount of a compound that inhibits miRNA expression is an amount sufficient to result in a biological effect (such as alleviating one or more signs or symptoms of IBS). For example, an agent can decrease the expression level of a target miRNA listed in Table 1 by a desired amount, for example by at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, 2-fold, at least 3-fold, at least 4-fold, or at least 5-fold, relative to a control or reference value.

One skilled in the art can readily determine a therapeutically effective amount of an agent to be administered to a given subject by taking into account several factors, such as the size and weight of the subject; the extent of disease progression; the age, health and sex of the subject; the route of administration; and whether the administration is regional or systemic. One skilled in the art can also readily determine an appropriate dosage regimen for administering to a subject an agent that inhibits expression of miRNA gene product.

In some embodiments, a single agent that inhibits expression of a miRNA gene product is administered to the subject in need of treatment. In other embodiments, two or more agents (such as 2, 3, 4, 5, 6, 7, 8, 9 or 10 or more) that inhibit expression of a miRNA gene product are administered to the subject. When two or more agents are administered to the subject, the agents can be administered simultaneously (or within quick succession, such as within minutes of each other), or they can be administered at different times. For example, two or more agents can be administered one hour, twelve hours, one day, two days, five days, one week, two weeks or one month apart.

In some embodiments, an agent that inhibits miRNA expression can be administered to a subject in combination with one or more additional treatments for IBS.

An agent that inhibits expression of a miRNA gene product can be any type of compound, such as, but not limited to, a nucleic acid molecule, polypeptide, antibody or small molecule, that is capable of inhibiting expression of one or more miRNA gene products. In some embodiments, the agent is an antisense compound.

Any type of antisense compound that specifically targets a miRNA gene product is contemplated for use to inhibit expression of the target miRNA gene product. In some examples, the agent is an antisense compound selected from an antisense oligonucleotide, a siRNA, or a ribozyme. Methods of designing, preparing and using antisense compounds are within the abilities of one of skill in the art. Furthermore, sequences for the disclosed miRNA gene products are publicly available. Antisense compounds specifically targeting a miRNA that is differentially expressed in IBS (or other target nucleic acid) can be prepared by designing compounds that are complementary to the target nucleotide sequence, such as a pri-miRNA, pre-miRNA or mature miRNA sequence. Antisense compounds need not be 100% complementary to the target nucleic acid molecule to specifically hybridize with the target nucleic acid molecule. For example, the antisense compound, or antisense strand of the compound if a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Patent Application Publication No. 2003/0228689, which is incorporated by reference herein in its entirety).

In some embodiments, the antisense compounds are antisense oligonucleotides. The miRNA gene product-specific antisense oligonucleotides can be any suitable length to allow for hybridization and modulation of gene expression. The length of an antisense oligonucleotide can vary, but is typically about 15 to about 40 nucleotides. In some embodiments, the antisense oligonucleotides are about 20 to about 35 nucleotides in length. The antisense oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. Oligonucleotide modifications are described in detail below.

In other embodiments, the antisense compounds are siRNA molecules. siRNAs useful for the disclosed methods include short double-stranded RNA from about 17 nucleotides to about 29 nucleotides in length, preferably from about 19 to about 25 nucleotides in length, such as about 21 to about 23 nucleotides in length. The siRNAs are made up of a sense RNA strand and a complementary antisense RNA strand annealed together by standard Watson-Crick base-pairing interactions. The sense strand includes a nucleic acid sequence that is substantially identical to a nucleic acid sequence contained within the target miRNA gene product. As used herein, a siRNA nucleic acid sequence that is "substantially identical" to a target sequence is a nucleic acid sequence that is identical to the target sequence, or that differs from the target sequence by one, two or three nucleotides. The sense and antisense strands of the siRNA can either include two complementary, single-stranded RNA molecules, or can be a single molecule having two complementary portions (which are base-paired) separated a single-stranded "hairpin" region.

The siRNA can also be altered RNA that differs from naturally-occurring RNA by the addition, deletion, substitution and/or alteration of one or more nucleotides. Such alterations can include addition of non-nucleotide material, such as to one or both of the ends of the siRNA or to one or more internal nucleotides of the siRNA; modifications that make the siRNA resistant to nuclease digestion; or the substitution of one or more nucleotides in the siRNA with deoxyribonucleotides. One or both strands of the siRNA can also include a 3' overhang. As used herein, a "3' overhang" refers to at least one unpaired nucleotide extending from the 3'-end of a duplexed RNA strand. Thus, in certain embodiments, the siRNA includes at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA and is 2 nucleotides in length. For example, each strand of the siRNA can comprise 3' overhangs of dithymidylic acid ("TT") or diuridylic acid ("uu").

In other embodiments, the antisense compound is a ribozyme. Ribozymes are nucleic acid molecules having a substrate binding region that is complementary to a contiguous nucleic acid sequence of a miRNA gene product, and which is able to specifically cleave the miRNA gene product. The substrate binding region need not be 100% complementary to the target miRNA gene product. For example, the substrate binding region can be, for example, at least about 50%, at least about 75%, at least about 85%, or at least about 95% complementary to a contiguous nucleic acid sequence in a miRNA gene product. The enzymatic nucleic acids can also include modifications at the base, sugar, and/or phosphate groups.

Antisense compounds, such as antisense oligonucleotides, siRNAs and ribozymes, can be produced chemically or biologically, or can be expressed from a recombinant plasmid or viral vector, as described in further detail below in regard to expression of isolated miRNA gene products. Exemplary methods for producing and testing antisense compounds are well known in the art (see, for example, U.S. Pat. Nos. 5,849,902 and 4,987,071; U.S. Patent Application Publication Nos. 2002/0173478 and 2004/0018176; Stein and Cheng, Science 261:1004, 1993; Werner and Uhlenbeck, *Nucl. Acids Res.* 23:2092-2096, 1995; Hammann et al., *Antisense and Nucleic Acid Drug Dev.* 9:25-31).

In some examples, the antisense compounds specific for a miRNA gene product contain one or more modifications to enhance nuclease resistance and/or increase activity of the compound. Modified antisense compounds include those comprising modified backbones or non-natural internucleoside linkages. As defined herein, oligonucleotides having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Modified oligonucleotides can also contain one or more substituted sugar moieties. In some examples, the oligonucleotides can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense compounds comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., *Helv. Chim. Acta.,* 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethoxyethyl or 2'-DMAEOE).

Similar modifications can also be made at other positions of the compound. Antisense compounds can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

B. Agents that Increase Down-Regulated miRNAs

Also provided is a method of treating a subject with IBS by administering to the subject a therapeutically effective amount of an isolated miRNA gene product that is down-regulated in a subject with a IBS, relative to a control (such as a healthy subject). The miRNA gene product can be a pri-miRNA, a pre-miRNA or a mature miRNA.

The disclosed methods comprise administering a therapeutically effective amount of at least one isolated miRNA gene product, or an isolated variant or biologically-active fragment thereof. The isolated miRNA gene product that is administered to the subject can be identical to an endogenous wild-type miRNA gene product (such as a pri-miRNA, pre-miRNA or mature miRNA) that is down-regulated in the subject with IBS, or it can be a variant or biologically-active fragment thereof. As defined herein, a "variant" of a miRNA gene product refers to a miRNA that has less than 100% identity to a corresponding wild-type miRNA gene product and possesses one or more biological activities of the corresponding wild-type miRNA gene product. Examples of such biological activities include, but are not limited to, inhibition of expression of a target RNA molecule (e g, inhibiting translation of a target RNA molecule, modulating the stability of a target RNA molecule, or inhibiting processing of a target RNA molecule) and inhibition of a cellular process associated with IBS. These variants include species variants and variants that are the consequence of one or more mutations (e.g., a substitution, a deletion, an insertion) in a miRNA gene. In certain embodiments, the variant is at least about 70%, at least about 75%, at least about 80%, at least about 85%, at least about 90%, at least about 95%, at least about 98%, or at about 99% identical to a corresponding wild-type miRNA gene product.

As used herein, a "biologically-active fragment" of a miRNA gene product refers to an RNA fragment of a miRNA gene product that possesses one or more biological activities of a corresponding wild-type miRNA gene product. As described above, examples of such biological activities include, but are not limited to, inhibition of expression of a target RNA molecule and inhibition of a cellular process associated with IBS. In certain embodiments, the biologically-active fragment is at least about 9, at least about 11, at least about 13, at least about 15, at least about 17 or at least about 19 nucleotides in length.

A therapeutically effective amount of an isolated gene product can be, for example, the amount necessary to alleviate one or more signs or symptoms of IBS, and/or the amount required to delay progression of the disease. One of skill in the art can determine the amount of an isolated miRNA gene product required for therapeutic efficacy.

In some embodiments, a single isolated miRNA gene product is administered to the subject in need of treatment. In other embodiments, two or more miRNA gene products (such as 2, 3, 4, 5, 6, 7, 8, 9 or 10 or more) are administered to the subject. When two or more miRNA gene products are administered to the subject, the miRNA gene products can be administered simultaneously (or within quick succession, such as within minutes of each other), or they can be administered at different times. For example, two or more miRNA gene products can be administered one hour, twelve hours, one day, two days, five days, one week, two weeks or one month apart.

In some embodiments, an isolated miRNA gene product can be administered to a subject in combination with one or more additional treatments for IBS. Exemplary treatments include are known to the person of skill in the art.

As used herein, an "isolated" miRNA gene product is one that is synthesized, or is purified away from other biological components of the cell or tissue in which the miRNA naturally occurs. For example, a synthetic miRNA gene product, or a miRNA gene product partially or completely separated from the other biological components of its natural state is considered to be "isolated." Isolated miRNA gene products can be obtained using a number of standard techniques. For example, the miRNA gene products can be chemically synthesized or recombinantly produced using methods known in the art. In one embodiment, miRNA gene products are chemically synthesized using appropriately protected ribonucleoside phosphoramidites and a conventional DNA/RNA synthesizer. Commercial suppliers of synthetic RNA molecules or synthesis reagents include, for example, Proligo (Hamburg, Germany), Dharmacon Research (Lafayette, Colo.), Pierce Chemical (Rockford, Ill.), Glen Research (Sterling, VS), ChemGenes (Ashland, Mass.) and Cruachem (Glasgow, United Kingdom).

In some embodiments, the method includes administering a vector encoding a miRNA gene product. Vectors can be of non-viral (for example, plasmids) or viral (for example, adenovirus, adeno-associated virus, retrovirus, herpes virus, vaccinia virus) origin. Suitable vectors, such as gene therapy vectors, are well known in the art.

In some examples, the miRNA gene products are expressed from recombinant circular or linear DNA plasmids using any suitable promoter. Suitable promoters for expressing RNA from a plasmid include, for example, the U6 or H1 RNA pol III promoter sequences, or a cytomegalovirus promoter. Selection of other suitable promoters is within the skill in the art. The recombinant plasmids of the invention can also comprise inducible or regulatable promoters for expression of the miRNA gene products.

When two or more miRNA gene products are to be expressed, the miRNA gene products can each be expressed from separate recombinant plasmids, or they can be expressed from the same recombinant plasmid. In one embodiment, the miRNA gene products are expressed as RNA precursor molecules from a single plasmid, and the precursor molecules are processed into the functional miRNA gene product within the target cell. Selection of plasmids suitable for expressing the miRNA gene products, methods for inserting nucleic acid sequences into the plasmid to express the gene products, and methods of delivering the recombinant plasmid to the cells of interest are within the skill in the art (see, for example, Zeng et al., *Mol. Cell* 9:1327-1333, 2002; Tuschl, Nat. Biotechnol., 20:446-448, 2002; Brummelkamp et al., *Science* 296:550-553, 2002; Miyagishi et al., *Nat. Biotechnol.* 20:497-500, 2002; Paddison et al., *Genes Dev.* 16:948-958, 2002; Lee et al., *Nat. Biotechnol.* 20:500-505, 2002; and Paul et al., *Nat. Biotechnol.* 20:505-508, 2002). In one embodiment, a plasmid expressing the miRNA gene product comprises a sequence encoding a miRNA precursor RNA operably linked to the CMV intermediate-early promoter.

The miRNA gene products can also be expressed from recombinant viral vectors. When administering two or more miRNA gene products, it is contemplated that the miRNA gene products can be expressed from two separate recombinant viral vectors, or from the same viral vector. The RNA expressed from the recombinant viral vectors can either be isolated from cultured cell expression systems by standard techniques, or can be expressed directly in target cells or tissues of a subject with IBS.

The recombinant viral vectors of use with the disclosed methods include sequences encoding the miRNA gene products and any suitable promoter for expressing the RNA sequences. Suitable promoters include, but are not limited to, the U6 or H1 RNA pol III promoter sequences, or a cytomegalovirus promoter. Selection of other suitable promoters is within the skill in the art. The recombinant viral vectors of the invention can also comprise inducible or regulatable promoters for expression of the miRNA gene products.

Suitable viral vectors include, but are not limited to, adenovirus vectors, adeno-associated virus vectors, retroviral vectors, lentiviral vectors, herpesviral vectors, and the like. For example, adenovirus vectors can be first, second, third and/or fourth generation adenoviral vectors or gutless adenoviral vectors. Adenovirus vectors can be generated to very high titers of infectious particles; infect a great variety of cells; efficiently transfer genes to cells that are not dividing; and are seldom integrated in the host genome, which avoids the risk of cellular transformation by insertional mutagenesis (Zern and Kresinam, Hepatology 25(2), 484-491, 1997). Representative adenoviral vectors which can be used for the methods provided herein are described by Stratford-Perricaudet et al. (*J. Clin. Invest.* 90: 626-630, 1992); Graham and Prevec (In *Methods in Molecular Biology: Gene Transfer and Expression Protocols* 7: 109-128, 1991); and Barr et al. (*Gene Therapy,* 2:151-155, 1995).

Adeno-associated virus (AAV) vectors also are suitable for administration of HCC-associated genes. Methods of generating AAV vectors, administration of AAV vectors and their use are well known in the art (see, for example, U.S. Pat. No. 6,951,753; U.S. Pre-Grant Publication Nos. 2007-036757, 2006-205079, 2005-163756, 2005-002908; and PCT Publication Nos. WO 2005/116224 and WO 2006/119458).

Retrovirus, including lentivirus, vectors can also be used with the methods described herein. Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289).

Suitable herpesvirus vectors can be derived from any one of a number of different types of herpesviruses, including, but not limited to, herpes simplex virus-1 (HSV-1), HSV-2 and herpesvirus saimiri. Recombinant herpesvirus vectors, their construction and uses are well described in the art (see, for example, U.S. Pat. Nos. 6,951,753; 6,379,6741 6,613, 892; 6,692,955; 6,344,445; 6,319,703; and 6,261,552; and U.S. Patent Application Publication No. 2003-0083289).

One skilled in the art can readily determine an effective amount of a miRNA gene product to be administered to a given subject, by taking into account factors, such as the size and weight of the subject; the extent of disease progression; the age, health and sex of the subject; the route of administration; and whether the administration is regional or systemic.

For example, an effective amount of an isolated miRNA gene product can be based on the approximate body weight of a subject to be treated. Such effective amounts can be administered by any suitable route, such as, for example, parenterally or enterally. In some examples, an effective amount of the isolated miRNA gene product that is administered to a subject can range from about 5 to about 3000 micrograms/kg of body weight, from about 700 to about 1000 micrograms/kg of body weight, or greater than about 1000 micrograms/kg of body weight.

One skilled in the art can also readily determine an appropriate dosage regimen for the administration of an isolated miRNA gene product to a given subject. For example, a miRNA gene product can be administered to the subject once (e.g., as a single injection or deposition). Alternatively, a miRNA gene product can be administered once or twice daily to a subject for a period of from about three to about twenty-eight days, more particularly from about seven to about ten days. In a particular dosage regimen, a miRNA gene product is administered once a day for seven days. Where a dosage regimen comprises multiple administrations, it is understood that the effective amount of the miRNA gene product administered to the subject can comprise the total amount of gene product administered over the entire dosage regimen.

C. Additional Agents for Treating IBS

In several embodiments, a subject with IBS is identified using the diagnostic methods disclosed herein, and the subject is administered one or more therapeutic agents to treat the IBS. For example, if a subject is identified as a subject with IBS with constipation, the subject can be administered a therapeutically effective amount of an agent that treats IBS with constipation. If a subject is identified as a subject with IBS with diarrhea, the subject can be administered a therapeutically effective amount of an agent that treats IBS with diarrhea.

Any suitable agent for the treatment or prevention of IBS can be administered to a subject as part of a treatment regimen that includes inhibiting or treating IBS. Suitable drugs that are useful for treating one or more symptoms associated with IBS include, but are not limited to, serotonergic agents, antidepressants, chloride channel activators, chloride channel blockers, guanylate cyclase agonists, antibiotics, opioids, neurokinin antagonists, antispasmodic or anticholinergic agents, *belladonna* alkaloids, barbiturates, glucagon-like peptide-1 (GLP-1) analogs, corticotropin releasing factor (CRF) antagonists, probiotics, free bases thereof, pharmaceutically acceptable salts thereof, derivatives thereof, analogs thereof, and combinations thereof.

Other IBS drugs include bulking agents, dopamine antagonists, carminatives, tranquilizers, dextofisopam, phenyloin, timolol, and diltiazem.

Serotonergic agents are useful for the treatment of IBS symptoms such as constipation, diarrhea, and/or alternating constipation and diarrhea. Non-limiting examples of serotonergic agents are described in Cash et al., *Aliment. Pharmacol. Ther.*, 22:1047-1060 (2005), and include 5-HT$_3$ receptor agonists (e.g., MKC-733, etc.), 5-HT4 receptor agonists (e.g., tegaserod (Zelnorm™), prucalopride, AG1-001, etc.), 5-HT$_3$ receptor antagonists (e.g., alosetron (Lotronex®), cilansetron, ondansetron, granisetron, dolasetron, ramosetron, palonosetron, E-3620, DDP-225, DDP-733, etc.), mixed 5-HT$_3$ receptor antagonists/5-HT4 receptor agonists (e.g., cisapride, mosapride, renzapride, etc.), free bases thereof, pharmaceutically acceptable salts thereof, derivatives thereof, analogs thereof, and combinations thereof. Additionally, amino acids like glutamine and glutamic acid which regulate intestinal permeability by affecting neuronal or glial cell signaling can be administered to treat subjects with IBS.

Antidepressants such as selective serotonin reuptake inhibitor (SSRI) or tricyclic antidepressants are particularly useful for the treatment of IBS symptoms such as abdominal pain, constipation, and/or diarrhea. Non-limiting examples of SSRI antidepressants include citalopram, fluvoxamine, paroxetine, fluoxetine, sertraline, free bases thereof, pharmaceutically acceptable salts thereof, derivatives thereof, analogs thereof, and combinations thereof. Examples of tricyclic antidepressants include, but are not limited to, desipramine, nortriptyline, protriptyline, amitriptyline, clomipramine, doxepin, imipramine, trimipramine, maprotiline, amoxapine, clomipramine, free bases thereof, pharmaceutically acceptable salts thereof, derivatives thereof, analogs thereof, and combinations thereof.

Chloride channel activators are useful for the treatment of IBS symptoms such as constipation. A non-limiting example of a chloride channel activator is lubiprostone (Amitiza™), a free base thereof, a pharmaceutically acceptable salt thereof, a derivative thereof, or an analog thereof. In addition, chloride channel blockers such as crofelemer are useful for the treatment of IBS symptoms such as diarrhea. Guanylate cyclase agonists such as MD-1100 are useful for the treatment of constipation associated with IBS (see, e.g., Bryant et al., *Gastroenterol.*, 128:A-257 (2005)). Antibiotics such as neomycin can also be suitable for use in treating constipation associated with IBS (see, e.g., Park et al., *Gastroenterol.*, 128:A-258 (2005)). Non-absorbable antibiotics like rifaximin (Xifaxan™) are suitable to treat small bowel bacterial overgrowth and/or constipation associated with IBS (see, e.g., Sharara et al., *Am. J. Gastroenterol.*, 101:326-333 (2006)).

Opioids such as kappa opiods (e.g., asimadoline) may be useful for treating pain and/or constipation associated with IBS. Neurokinin (NK) antagonists such as talnetant, saredutant, and other NK2 and/or NK3 antagonists may be useful for treating IBS symptoms such as oversensitivity of the muscles in the colon, constipation, and/or diarrhea. Antispasmodic or anticholinergic agents such as dicyclomine may be useful for treating IBS symptoms such as spasms in the muscles of the gut and bladder. Other antispasmodic or anticholinergic agents such as *belladonna* alkaloids (e.g., atropine, scopolamine, hyoscyamine, etc.) can be used in combination with barbiturates such as phenobarbital to reduce bowel spasms associated with IBS. GLP-1 analogs such as GTP-010 may be useful for treating IBS symptoms such as constipation. CRF antagonists such as astressin and probiotics such as VSL#3® may be useful for treating one or more IBS symptoms. One skilled in the art will know of additional IBS drugs currently in use or in development that are suitable for treating one or more symptoms associated with IBS.

When used in combination with the administration of one of the disclosed therapeutic agents targeting one or more of miRNAs associated with IBS, the additional treatment methods described above can be administered or performed prior to, at the same time, or following the disclosed therapy as appropriate for the particular subject, the additional symptoms associated with IBS and the specific combination of therapies.

D. Administration

Agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

In some embodiments, the therapeutic agent is a nucleic acid molecule, such as a miRNA gene product, a vector encoding a miRNA gene product, an antisense compound or a vector encoding an antisense compound. A nucleic acid-based therapeutic agent can be administered to a subject by any suitable route. In some examples, the agents are administered using an enteral or parenteral administration route. In the context of the present disclosure, a miRNA gene product or an antisense compound can be administered to the subject either as naked RNA or DNA in combination with a delivery reagent, or can be encoded by a recombinant plasmid or viral vector. Recombinant plasmids and viral vectors including sequences that express the miRNA gene products or antisense compounds, and techniques for delivering such plasmids and vectors to target cells, are well known in the art.

In some embodiments, liposomes are used to deliver a miRNA gene product or antisense compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369). In some embodiments, polymers can be used to deliver a miRNA gene product or antisense compound to a subject. Cationic lipids and polymers that can be used to deliver therapeutic RNA molecules have been described (see, for example, Zhang et al., *J Control Release*. 123(1):1-10, 2007; Vorhies et al., *Methods Mol Biol.* 480:11-29, 2009; and U.S. Patent Application Publication No. 2009/0306194). Polypeptide carriers can also be used to administer a miRNA gene product to a subject (see, for example, Rahbek et al., *J. Gene Med.* 10:81-93, 2008).

EXAMPLES

The following examples are provided to illustrate certain particular features and/or embodiments. These examples should not be construed to limit the disclosure to the particular features or embodiments described.

Example 1

Elevated Circulating miR-150 and miR-342-3p in Patients with Irritable Bowel Syndrome This example illustrates identification of a miRNA expression signature that is associated with IBS. The signature includes the expression levels of two miRNAs, including hsa-miR-150 and hsa-miR-342-3p. Detection of the expression signature in a subject can be used to identify the subject as a subject with IBS.

Materials and Methods

Sample. Patients who met Rome II criteria (i.e., chronic or recurrent abdominal pain, and altered stooling habits) for IBS (IBS-D=5, IBS-C=5, or IBS-M=2) and healthy controls (i.e., no known organic disease or gastrointestinal (GI) symptoms, n=31) were identified (clinicaltrial.gov #NCT00824921; see Table 1 for demographic and clinical indicators), at the National Institutes of Health (NIH) Hatfield Clinical Research Center. Whole blood samples were collected via venipuncture in PAXGene tubes (PreAnalytiX, Qiagen, Valencia, Calif., USA) as per the manufacturer's instructions, and stored at −80° C. until RNA purification.

miRNA Expression. Total RNA, including miRNA, was extracted using the PAXGene Blood miRNA extraction kit (PreAnalytiX, Qiagen, Valencia, Calif., USA). The nCounter Human miRNA Expression Assay Kit V1.4 (NanoString Technologies, Seattle, Wash., USA) was used to anneal miRNAs to target specific barcode probes. No amplification was required. The sample was then immobilized on an nCounter Cartridge using the nCounter Prep Station. Barcode probes were counted and recorded for each miRNA target (735 human miRNAs) using the nCounter Digital Analyzer. The data were normalized to the top 100 expressed miRNAs, and the background was corrected using the nSolver software package. A 25 count threshold was set. miRNA species with more than 75% of cases at this threshold were excluded as such low counts cannot be accurately reproduced. Using these criteria 138 miRNAs were included in subsequent analyses. Repeated samples and internal controls show a high degree of consistency between assays.

Statistical Analysis. Statistical analysis of the demographic and clinical data was performed using SPSS v15.0 with a priori statistical significance set at p≤0.05. Comparisons of each parameter were conducted using the parametric independent sample Student's t-test. Statistical analysis of the genetic data was performed using BRB-Array Tools (Biometric Research Branch, National Cancer Institute) with the a priori statistical significance set at p≤0.05. A priori p-values were adjusted for False Discovery Rate (FDR). miRNA data from IBS patients and healthy controls were compared while assessing the presence of race and gender effects. Integrated Pathway Analysis (IPA, Ingenuity Systems, Inc.) was used to explore the functional associations of miRNA species of interest.

Results

Demographic and Clinical Data. The IBS group was not significantly different in terms of age, body mass index (BMI), hematocrit, C-reactive protein (CRP), erythrocyte sedimentation rate (ESR), alanine transaminase (ALT), aspartate aminotransferase (AST), or amylase compared to healthy controls (Table 2). Lipase was significantly higher in IBS patients compared to healthy controls (Table 2). Although a difference in lipase was observed among groups, none of the values fell outside of the normal clinical range for these indices.

TABLE 2

Demographic and clinical characteristics of human subjects.

| Variable | Healthy Controls (n = 31) | IBS Patients (n = 12) | P Value |
|---|---|---|---|
| Gender (n) | | | |
| Male | 15 | 3 | — |
| Female | 16 | 9 | — |
| Race (n) | | | |
| Asian | 7 | 2 | — |
| African American/Black | 13 | 8 | — |
| Caucasian | 7 | 1 | — |
| Other | 4 | 1 | — |
| Age | 27.9 ± 8.5 | 29.2 ± 7 | p > 0.05 |
| Range (yr) | 13-45 | 16-45 | |
| IBS-D | — | 5 | |
| IBS-C | — | 5 | |
| IBS-M | — | 2 | |
| BMI | 24.5 ± 4.7 | 26.6 ± 5.8 | p > 0.05 |
| Range (Kg/m$^2$) | 28.5-48.2 | 20.5-41.3 | |
| Hematocrit | 40.4 ± 5.0 | 39.4 ± 4.6 | p > 0.05 |
| Range (%) | 28.5-48.2 | 30.2-47.9 | |
| CRP | 1.8 ± 1.8 | 3.1 ± 4.8 | p > 0.05 |
| Range (mg/L) | 0.2-7.3 | 0.2-17.5 | |
| ESR | 9.6 ± 8.4 | 12.5 ± 7.7 | p > 0.05 |
| Range (mm/hr) | 2.0-30.0 | 3.0-25.0 | |
| Alk. Phos. | 75.2 ± 56.6 | 66.0 ± 19.6 | p > 0.05 |
| Range (U L$^{-1}$) | 36.0-367.0 | 40.0-110.0 | |
| ALT | 27.5 ± 10.6 | 28.6 ± 13.7 | p > 0.05 |
| Range (U L$^{-1}$) | 15.0-66.0 | 17.0-55.0 | |
| AST | 17.8 ± 8.9 | 20.5 ± 15.0 | p > 0.05 |
| Range (U L$^{-1}$) | 6.0-53.0 | 6.0-61.0 | |
| GGTP | 25.0 ± 12.6 | 34.2 ± 28.3 | p > 0.05 |
| Range (U L$^{-1}$) | 9.0-57.0 | 11.0-113.0 | |
| Amylase | 64.5 ± 20.8 | 71.4 ± 20.9 | p > 0.05 |
| Range (U L$^{-1}$) | 29.0-117.0 | 46.0-109.0 | |
| Lipase | 127.6 ± 46.5 | 168.5 ± 72.3 | p = 0.034 |
| Range (U L$^{-1}$) | 63.0-255.0 | 85.0-357.0 | |

Figure 1B:
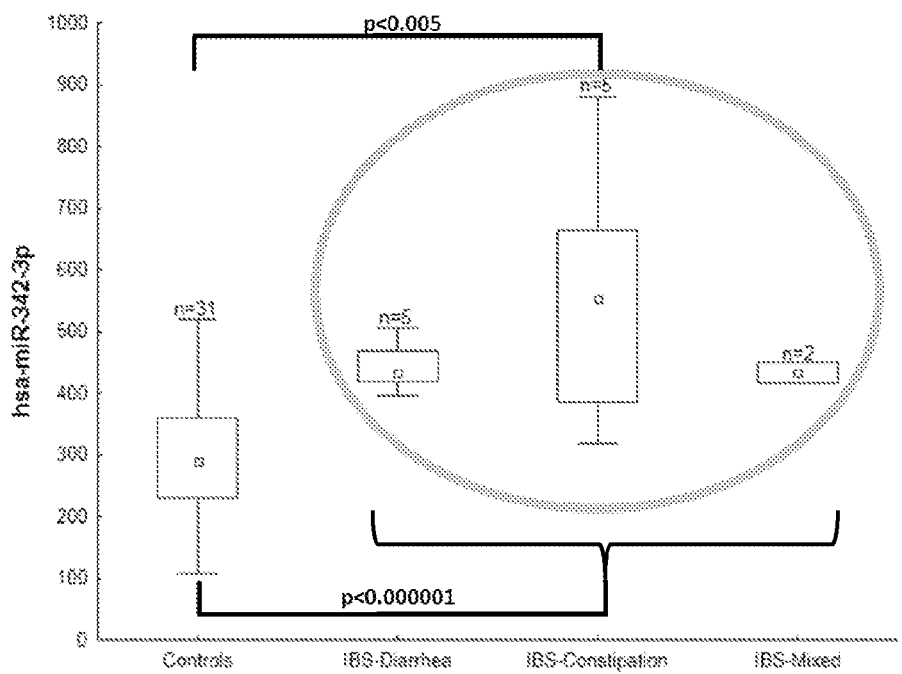

With reference to Table 2, the following abbreviations are used: Alk. Phos, alkaline phosphatase; ALT, alanine transaminase; AST, aspartate aminotransferase; BMI, body mass index; CRP, C-reactive protein; ESR, erythrocyte sedimentation rate; GGTP, gamma glutamyl transpeptidase IBS, irritable bowel syndrome; IBS-C, irritable bowel syndrome constipation; IBS-D, irritable bowel syndrome diarrhea; IBS-M, irritable bowel syndrome mixed.

miRNA Expression. Both hsa-miR-150 and hsa-miR-342-3p were found to be elevated (FDR adjusted p≤0.05) in patients with IBS compared to healthy controls (FIGS. 1A and 1B). The expression of hsa-miR-150 and hsa-miR-342-3p were 1.6 and 1.7 fold higher, respectively, in IBS patients (mean±1 standard deviation: hsa-miR-150=3988±1195; hsa-miR-342-3p=491±152) than in healthy controls (hsa-miR-150=2509±1135; hsa-miR-342-3p=292±87). The IBS-constipation (hsa-miR-342-3p=560±225) cohort but not the IBS-diarrhea (hsa-miR-342-3p=444±44) cohort had elevated (p<0.005) hsa-miR-342-3p expression compared to healthy controls (FIG. 1B). Expression of these miRNAs was not found to have any relationship to race or gender.

Figure 2:
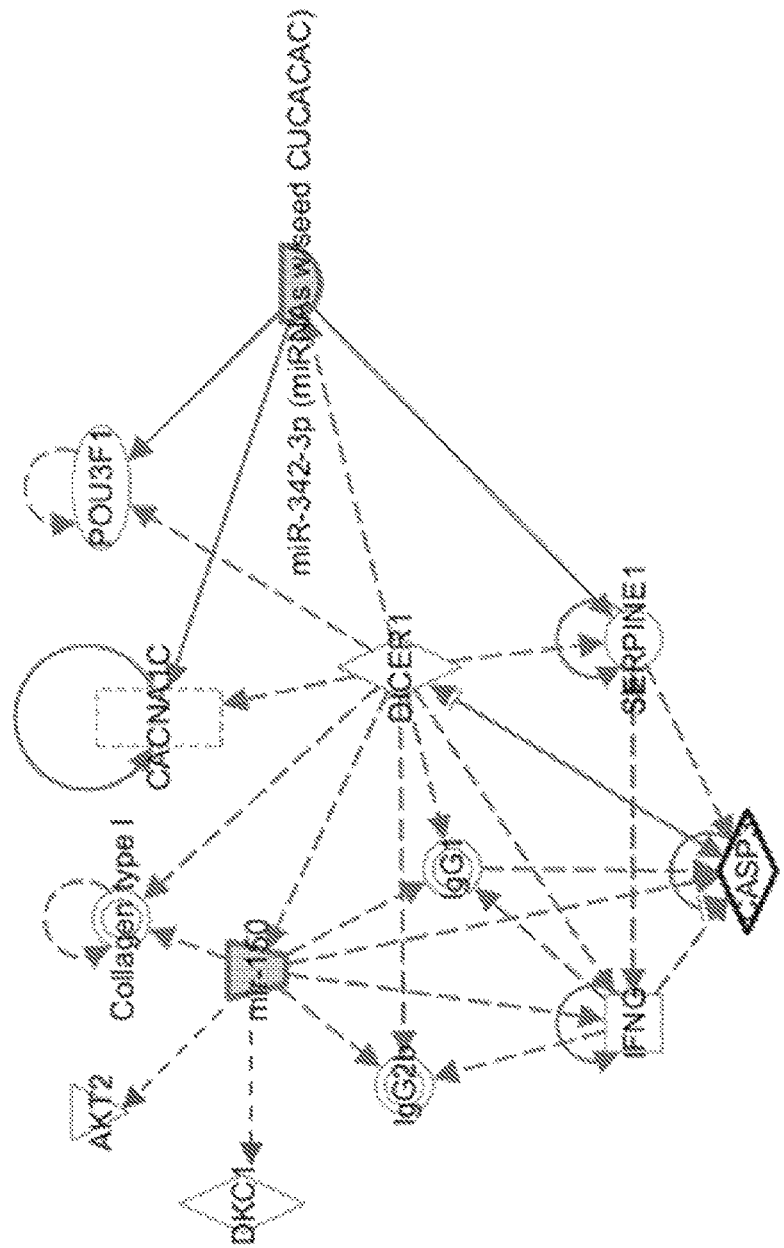
FIG. 2 shows an Integrated Pathway Analysis (IPA) network outlining relationships between hsa-miR-342-3p and hsa-miR-150 and related miRNAs and proteins. Direct and indirect relationships are shown by solid and dashed lines, respectively. The arrow indicates specific directionality of interactions.

Integrated Pathway Analysis of IBS-Associated miRNAs. To explore possible interactions of these miRNAs with other genes and proteins, and their role in different molecular pathways, they were entered into an Ingenuity Pathway Analysis (IPA; Ingenuity Systems Inc., Redwood City, Calif.). The analysis merged networks associated with the following diseases: cancer, hematological disease, organismal injury and abnormalities, endocrine system disorders, and reproductive system disease. In addition, functional networks related to cellular development, growth, proliferation, movement, death, survival, and cell-to-cell signaling were merged. Several genes with both direct and indirect bindings to the two miRNA species were revealed, including the calcium channel voltage-dependent L type alpha 1C subunit (CACNA 1C), caspase-3, and the serine-threonine protein kinase AKT2 (FIG. 2).

Discussion

Hsa-miR-150 and hsa-miR-342-3p were identified as up-regulated in IBS patients compared to healthy controls. Despite the small sample size, a consistent differential expression of hsa-miR-342-3p between the different IBS-subtypes (diarrhea, constipation, or mixed) compared to healthy controls is evident. Neither race nor gender was found to explain variation in these miRNAs.

The hsa-miR-342-3p has been found to be up-regulated in Bladder Pain Syndrome (BPS) (Gheinani et al., 2013. Cell Mol Life Sci. 70, 3773-3789). Without being bound by theory, similar to the symptom of abdominal pain with unknown cause presenting in the IBS patients, BPS patients present with pelvic pain in the absence of a specific cause. The IPA provides a potential molecular link between this miRNA and pain signaling pathways by revealing an association with the voltage-dependent L type calcium channel alpha 1C protein (CACNA 1C). Regulated processing of the CACNA1 mRNA has been functionally associated with nociceptive pain transmission (Lipscombe et al., 2013. Biochimica et Biophysica Acta. 1828, 1522-1529). Dysregulated expression of L-type calcium channels is also associated with altered colonic motility and smooth muscle contraction in a rat model of IBS (Zhang et al., Neurogastroenterol Motil., 22, e162-170, 2010). In addition to chronic pain, inflammation also underlies the pathogenesis of BPS. It has been previously observed that inflammatory markers are disproportionately represented in colonic tissues from IBS patients, which suggests a sub-clinical inflammatory component in IBS (Henderson et al., 2012. World J. Gastrointest. Pathophysiol. 3, 102-108). Taken together, the functional role of the hsa-miR-342-3p may involve inflammatory, pain signaling, smooth muscle contractility, and GI tract motility pathways.

The hsa-miR-150 also has a postulated role in inflammation and has been previously associated with Crohn's disease (CD), ulcerative colitis (UC), and colorectal cancer (Ma et al., 2012. Gut. 61, 1447-53; Pekow et al., Inflamm Bowel Dis. 18, 187-193). This miRNA was found to be over expressed in the colon epithelium of patients with CD and UC (Pekow et al., Inflamm Bowel Dis. 18, 187-193) and has also been associated with pain (Orlova et al., 2011. J Transl Med. 9, 195-205). Targets of the hsa-miR-150 include the telomerase-related proteins Dyskerin (dyskeratosis congenita 1, DKC1), as well as AKT2, a pro-survival protein kinase activated via the PI3K pathway, and is expressed in many human malignancies. AKT, which is an important factor in inflammatory pathways, has also been linked to inflammatory bowel diseases (Anderson et al., 2010. Gastroenterology. 139, 718-722).

In summary, this example illustrates two miRNA species, hsa-miR-150 and hsa-miR-342-3p, that are differentially expressed in the peripheral circulation of patients suffering from IBS. Both miRNAs are implicated in inflammation and have previously been associated with pain.

Example 2

Dysregulation of Inflammatory miRNAs Associated with Gastrointestinal Symptoms in Irritable Bowel Syndrome This example illustrates identification of a miRNA expression signature that is associated with IBS. The signature includes the expression levels of six miRNAs, including hsa-miR-335, hsa-miR-574-3p, hsa-miR-342-3p, hsa-miR-151-3p, hsa miR-151-5p, and hsa-miR-362-5p). Detection of the expression signature in a subject can be used to identify the subject as a subject with IBS.

Materials and Methods

Human Subjects. Participants (n=20) were recruited into a natural history protocol (Protocol #09-NR-0064, PI: Henderson) and informed consent was obtained at the NIH Clinical Research Center. Caucasian patients (n=10) that fulfilled Rome III criteria for IBS with no other diagnosed organic disorders were compared to age-, gender-, race-, and weight-matched healthy controls (n=10, see Table 1 for demographic and clinical characteristics).

Sample Collection and miRNA Isolation. Peripheral whole blood was collected from fasting participants, stabilized in PAXgene® RNA tubes (PreAnalytiX) and stored at −80° C. until RNA processing. Total RNA extraction was carried out with the PAXgene® Blood miRNA kit (Qiagen) according to manufactures instructions.

miRNA Quantification. miRNAs were digitally counted using the nCounter® System (Nanostring®, Seattle Wash.). In summary, purified RNA was mixed with capture and reporter probes specific to each miRNA sequence. Sequences and probes are hybridized, and then immobilized on a surface. Next, the nCounter Digital Analyzer scans the surface and counts target-specific barcodes of each miRNA specific reporter probe (Collins et al., Annals of surgical oncology 21: 133-138, 2014; Fortina et al., Nature biotechnology 26: 293-294, 2008). miRNA sequence counts were background corrected and normalized using the nSolver™ software by NanoString Technologies, Seattle, Wash. The described procedures were carried out per manufacturer's instructions using nCounter® Human miRNA Expression Assay Kit V 1.4. Assays are designed with housekeeping genes, as well as positive and negative controls.

Data Analysis. Descriptive statistics of demographic and clinical data and miRNA counts were analyzed using SPSS version 15.0 (Chicago, Ill.). Analysis of miRNA counts were done using BRB-array tools version 3.6.0 (http://linus.nci.nih.gov/BRB ArrayTools.html). Counts of less than 10 were excluded from analysis, and miRNAs that had a less than a 75% call rate were excluded from subsequent analysis. A total of 196 miRNAs passed these filtering criteria and were used incomparative analysis. A randomized block design was used to compare IBS and control data in order to minimize any batch effects in the data. In order for differential expression in miRNAs to be considered statistically significance a priori p-values were set at $p \leq 0.05$ and the differential expression had to equal or exceed 1.5 fold. Integrated Pathway Analysis (IPA, Ingenuity Systems, Redwood City, Calif.) was completed on the significantly differentially expression miRNA species found between IBS and controls.

Results

Demographic and Clinical Characteristics of IBS and Control Patients. Ten Caucasian patients with chronic abdominal pain of greater than 6 months and who met the Rome III criteria for IBS were age-, gender-, race-, and weight-matched to ten healthy control individuals with no chronic abdominal pain and who did not have IBS. Overall, the IBS and control patient groups did not differ significantly on Body Mass index (BMI), hemoglobin, albumin, liver transaminases, C-reactive protein (CRP), and erythrocyte sedimentation rate (ESR) (Table 3).

TABLE 3

Demographic and clinical characteristics of human subjects.

| Variable | Overall (N = 20) | IBS Patients (n = 10) | Healthy Controls (n = 10) | P Value |
|---|---|---|---|---|
| Gender (n) | | | | |
| Male | 10 | 5 | 5 | — |
| Female | 10 | 5 | 5 | — |
| Race (n) | | | | |
| Caucasian | 20 | 10 | 10 | — |
| Age | 28.95 ± 7.44 | 27.50 ± 6.65 | 30.40 ± 8.25 | 0.40 |
| Range (yr) | (22-45) | (22-44) | (23-45) | |
| BMI | 25.44 ± 6.34 | 24.68 ± 4.42 | 26.21 ± 8.00 | 0.60 |
| Range (Kg/m$^2$) | (19-43) | (20-35) | (19-43) | |
| Hemoglobin | 14.05 ± 1.31 | 14.07 ± 1.74 | 14.03 ± 0.78 | 0.95 |
| Range (g/dL) | (10.90-16.70) | (10.90-16.70) | (12.60-15.00) | |
| Albumin | 4.11 ± 0.32 | 4.08 ± 0.41 | 4.13 ± 0.22 | 0.74 |
| Range (g/dL) | (3.70-4.90) | (3.70-4.90) | (3.80-4.40) | |
| CRP | 2.57 ± 3.91 | 3.71 ± 5.04 | 1.43 ± 2.00 | 0.20 |
| Range (mg/L) | (0.16-17.50) | (0.16-17.50*) | (0.16-6.47) | |
| ESR | 7.05 ± 5.86 | 7.70 ± 7.59 | 6.40 ± 3.75 | 0.63 |
| Range (mm) | (2.00-25.00) | (2.00-25.00) | (2.00-13.00) | |
| Liver Transaminases | | | | |
| ALT | 30.50 ± 13.50 | 32.20 ± 16.90 | 28.80 ± 9.62 | 0.59 |
| Range (U/L) | (18-77) | (18-77) | (18-44) | |
| AST | 18.85 ± 6.85 | 19.30 ± 6.98 | 18.40 ± 7.06 | 0.78 |
| Range (U/L) | (9-36) | (11-36) | (9-30) | |
| GGTP | 26.35 ± 13.69 | 29.80 ± 17.52 | 22.90 ± 7.91 | 0.27 |
| Range (U/L) | (15-62) | (15-62) | (15-40) | |

With reference to Table 3, all values expressed as mean±standard deviation (M±SD). BMI=Body Mass Index. Normal Clinical Range; Hemoglobin (12-18 g/dL), Albumin (3.5-5 g/dL), C-Reactive Protein (CRP, <10 mg/L), Erythrocyte Sedimentation Rate (ESR, 12-23 U/L), Alanine Aminotransferase (ALT, 6-41 U/L), Aspartate Aminotransferase (AST, 9-34 U/L), Gamma-Glutamyl Transpeptidase (GGTP, 5-85 U/L).

Figure 3A:
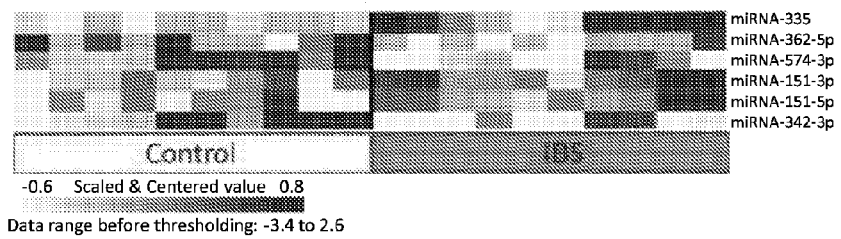
FIGS. 3A-3C illustrate altered expression of hsa-miR-335, hsa-miR-574-3p, hsa-miR-342-3p, hsa-miR-151-3p, hsa miR-151-5p, and hsa-miR-362-5p in IBS samples compared to control samples from healthy subjects.
Figure 3B:
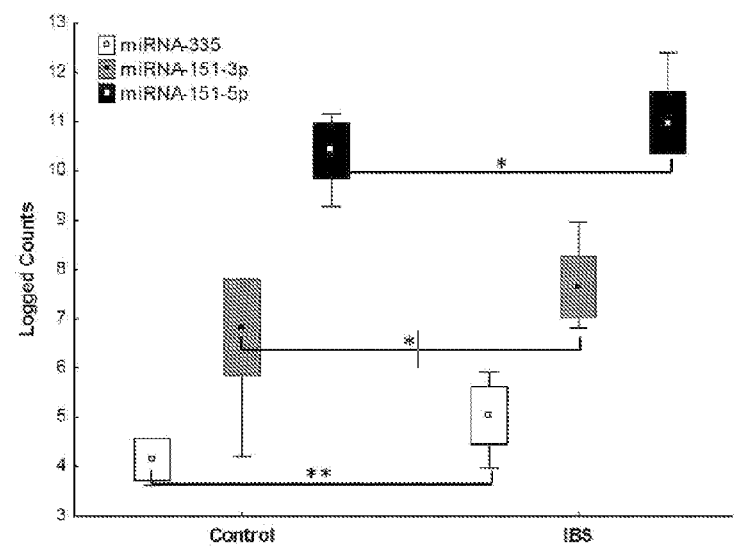
Figure 3C:
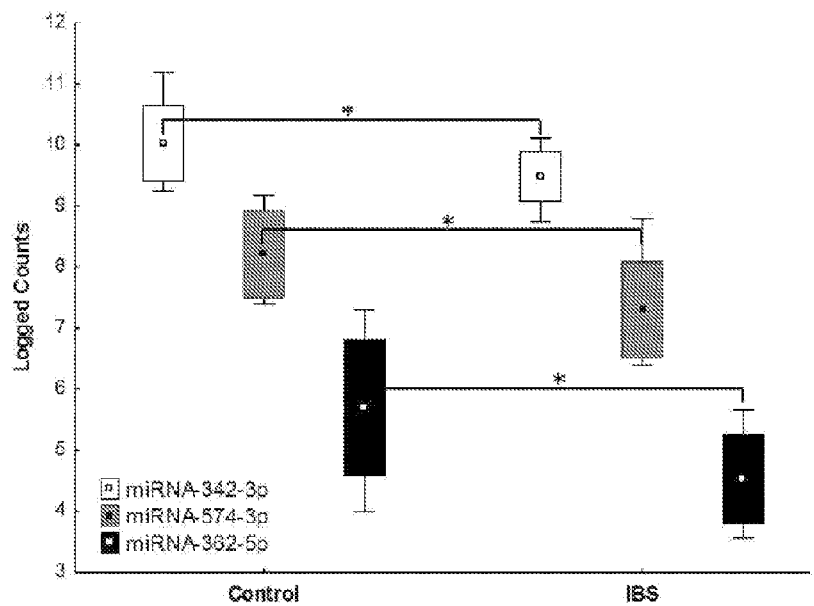

MiRNA Species and Expressions in IBS Versus Control Patients. Six human miRNAs (hsa-miR-335, hsa-miR-574-3p, hsa-miR-342-3p, hsa-miR-151-3p, hsa143 miR-151-5p, and hsa-miR-362-5p) were significantly differentially expressed ($p \leq 0.05$) and showed a relative fold change of 1.5 or more (Table 4 provides the statistical breakdown). A heatmap of significantly differentially expressed miRNAs is presented in FIG. 3A. Box and whisker plots of miRNAs that were significantly up-regulated (FIG. 3B) and down-regulated (FIG. 3C) when comparing IBS patients with matched controls are noted.

TABLE 4

Geometric mean counts, p-values and fold change of significantly differentially expressed miRNAs.

| miRNA | Parametric p-value | n | Geometric Mean - Control | n | Geometric Mean - IBS | Fold change in IBS versus control |
|---|---|---|---|---|---|---|
| Hsa-miRNA-335 | 0.004 | 5 | 18 | 10 | 33 | ↑1.9 |
| Hsa-miRNA-151-3p | 0.04 | 10 | 114 | 10 | 201 | ↑1.8 |
| Hsa-miRNA-151-5p | 0.04 | 10 | 1358 | 10 | 2016 | ↑1.5 |
| Hsa-miRNA-574-3p | 0.01 | 10 | 296 | 10 | 158 | ↓1.9 |
| Hsa-miRNA-342-3p | 0.04 | 10 | 1046 | 10 | 718 | ↓1.5 |
| Hsa-miRNA-362-5p | 0.05 | 7 | 52 | 8 | 23 | ↓2.3 |

Comparison of miRNAs Found to be Dysregulated in IBS Patients Versus Control with the Reported IBD-Associated miRNAs. The identified miRNA species were compared with miRNAs found by others to be dysregulated in IBD patients compared to control. Table 4 shows that the hsa-miR-151-5p and the hsa-miR-362-5p have been previously reported to be associated with IBD. The presence of these two miRNA species in the peripheral whole blood of Crohn's disease and ulcerative colitis patients distinguished these patient groups from healthy individuals (Wu et al., *Inflamm Bowel Dis* 17: 241-250, 2011).

TABLE 3

Comparison of the miRNAs found to be dysregulated in IBS patients versus control and the miRNAs reported to be dysregulated in IBD.

| miRNA | Fold change in IBS versus control | Dysregulation in IBD versus control |
| --- | --- | --- |
| Hsa-miRNA-335 | ↑1.9 | |
| Hsa-miRNA-151-3p | ↑1.8 | |
| Hsa-miRNA-151-5p | ↑1.5 | ↑in active CD and UC (Wu, et al., 2011) |
| Hsa-miRNA-574-3p | ↓1.9 | |
| Hsa-miRNA-342-3p | ↓1.5 | |
| Hsa-miRNA-362-5p | ↓2.3 | ↑ in active CD and UC (Wu, et al., 2011) |

CD = Crohn's Disease;
UC = Ulcerative Colitis

Figure 4:
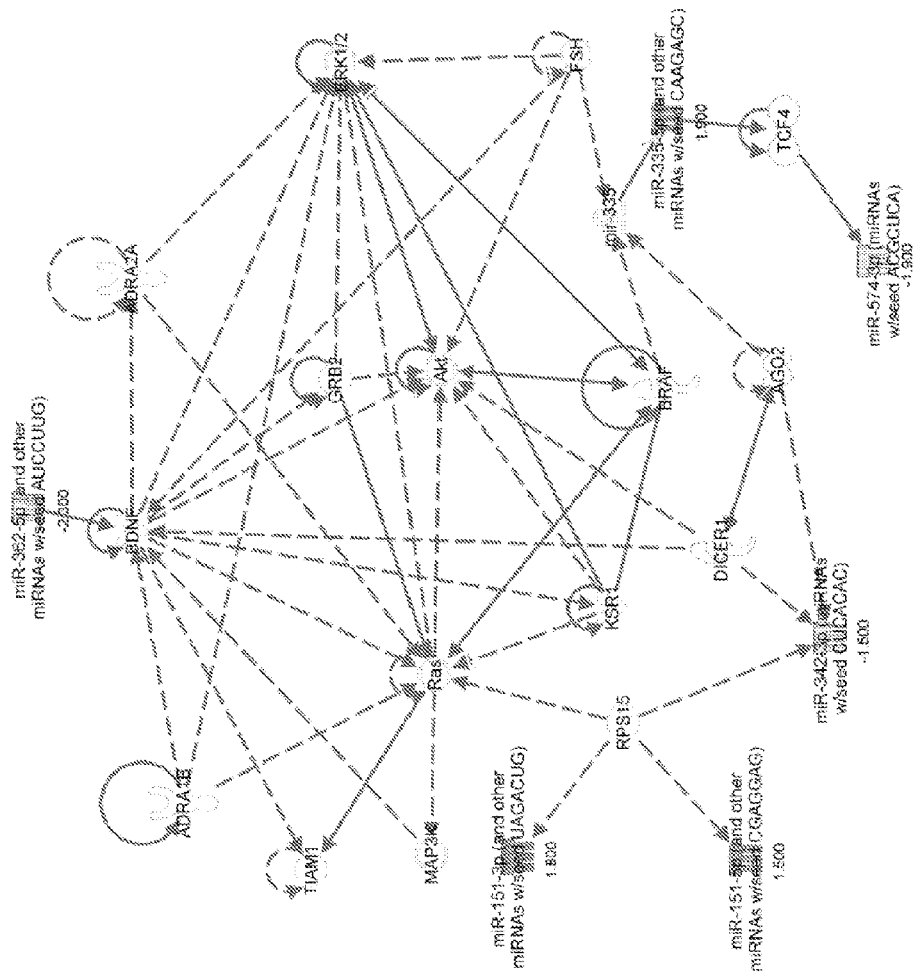
FIG. 4 shows an IPA network based on significantly differentially expressed miRNA molecules in IBS verses the control group. The fold change in miRNA expression is shown. Genes and miRNAs with no fold change indicated are added from the Ingenuity knowledge database. Direct and indirect relationships are shown by solid and dashed lines, respectively. The arrow indicates specific directionality of interactions.

Integrated Pathway Analysis of the Six miRNAs Found to be Dysregulated in IBS Patients Versus Control. The six identified human mature miRNAs were analyzed using Integrated Pathway Analysis (IPA, Ingenuity Systems, Redwood City, Calif. (FIG. 4)). The analysis merged networks associated with the following diseases: cancer, endocrine system disorders, reproductive system disease. In addition, functional networks related to hereditary disorders, neurological diseases, and cell morphology were merged. Several molecules were revealed and provided both direct and indirect links among the miRNA species analyzed, including Ras, Brain-Derived Neurotrophic Factor (BDNF), and Ribosomal Protein S15 (RPS15).

Discussion

The present pilot study identified six miRNA (miRNA) species that were dysregulated in patients with IBS compared to control individuals without IBS. The expressions of hsa-miR-335, hsa-miR-155-5p, and hsa-miR-155-3p were upregulated in IBS versus controls. On the other end of the spectrum, the expressions of hsa-miR-574-3p, hsa-miR-342-3p, and hsa-miR-362-5p were downregulated in IBS versus controls. The clinical and demographic characteristics of the IBS patient cohort were not significantly different from the healthy controls in terms of age, race, BMI, hemoglobin, albumin, liver transaminases, CRP, and ESR. This profile is important because it is a biological correlate to a symptom-based disease. To this end, biomarkers have been difficult to identify in IBS because of the elusive nature of the syndrome and the wide variety of symptoms. Here, it is shown that a group of detectable circulating miRNA species that may aid in diagnosis and also provide direction for future work in IBS.

Zhou and colleagues have shown a local effect of miRNA sequences in altering intestinal permeability (Zhou et al., Gut 59: 775-784, 2010). Here, that understanding of miRNA gene control is extended to circulating sequences and symptoms. These circulating sequences may provide insight into pathogenesis of IBS, as well circulating changes in IBS patients. In agreement with the current suggestion that low-grade inflammation contributes to IBS pathology (Vi-cario et al., Gut 59: 710-712, 2010), the circulating miRNA sequences identified here are linked to inflammatory pathways. The hsa-miR-151 family has also been shown to function in activating the Racland Cdc42 proteins, both of which are members of the Rho GTPase family and both contribute to inflammatory processes (Ding et al., Nat Cell Biol 12: 390-399, 2010). The contribution of Cdc42 to inflammation has recently been shown to be mediated via its function in controlling the polarity characteristic of neutrophils, which is needed for their migration along the chemotactic gradient in an inflamed microenvironment (Kumar et al., Blood 120: 3563-312 3574, 2012). Interestingly, a role in establishing a gradient for neutrophil and leukocyte migration has also been described for CCL-16, a chemokine gene previously reported to be differentially expressed in the same IBS versus control patient cohort studies in this example (Del Valle-Pinero et al., Neurogastroenterology and motility 23: 1092-1097, 2011; Starr et al., J Biol Chem 287: 5848-5860, 2012). A closer look of the miRNA sequences found in the patients further reveals speculative mechanisms beyond local inflammation. Dysregulation of the hsa196 miR-574-3p, hsa-miR-362-5p, and hsa-miR-151-3p has been associated with colorectal cancer (Nishida et al., Clin Cancer Res 18: 3054-3070, 2012). In hepatocellular carcinoma, the hsa-miR-151-5p expression is associated with increased tumor cell migration and invasion (Ding et al., Nat Cell Biol 12: 390-399, 2010).

It is noteworthy that while the molecular findings point to inflammation, the levels of clinical indices for inflammation (CRP and ESR) are not significantly different between IBS patients and control individuals. This suggests that molecular inflammatory signals, particularly those at moderate levels such as the ones identified here, may be missed by gross clinical laboratory analysis from peripheral blood. Jones et al. recently showed that among the serological markers examined in their study, only a small number of markers significantly differentiated IBS patients from healthy controls (9). Thus, in IBS assessment, in which the patients' self-reported symptoms are known to be highly variable and often vague, identification of micro-inflammatory signals such as miRNAs can potentially aid clinicians in making accurate diagnoses. MiRNA molecules isolated from an easily accessible patient specimen such as the peripheral whole blood may serve as ideal clinical tools due to their relatively stable nature Minimally invasive identification of an early inflammatory GI condition can also provide benefits in identifying patients on whom invasive GI diagnostic procedures may be recommended.

In summary, an association of six miRNA species with IBS has been identified. These miRNAs were significantly dysregulated in IBS patients with chronic abdominal pain of greater than 6 months compared to control individuals Inflammation appears to be the theme unifying the identified miRNAs, thus contributing to the ever-growing evidence of subclinical inflammation in IBS.

Example 3

Altered miRNA Expression in IBS and Control Samples

This example illustrates altered expression of miRNAs in IBS samples compared to control samples from healthy subjects, in IBS-D samples compared to healthy control samples, in IBS-C samples compared to healthy control samples, and in IBS-D samples compared to IBS-C samples. The results show gene expression signatures that can be used to distinguish between IBS, IBS-C, IBS-D, and healthy patients. Differentially expressed genes in each class comparison category were included in a stepwise discriminant functions analysis. An optimal combination of differentially expressed miRNAs that yielded high correct classification of both healthy controls and IBS (and IBS subtypes) was produced as a signature of the said condition.

Figure 7:
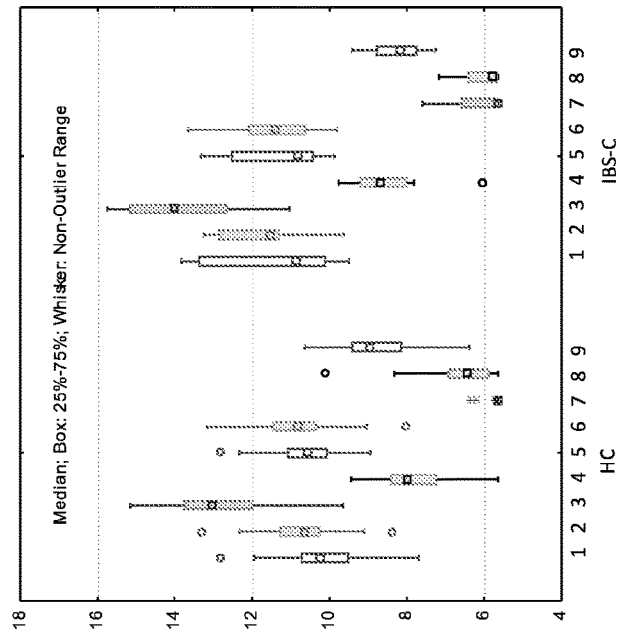
Figure 8:
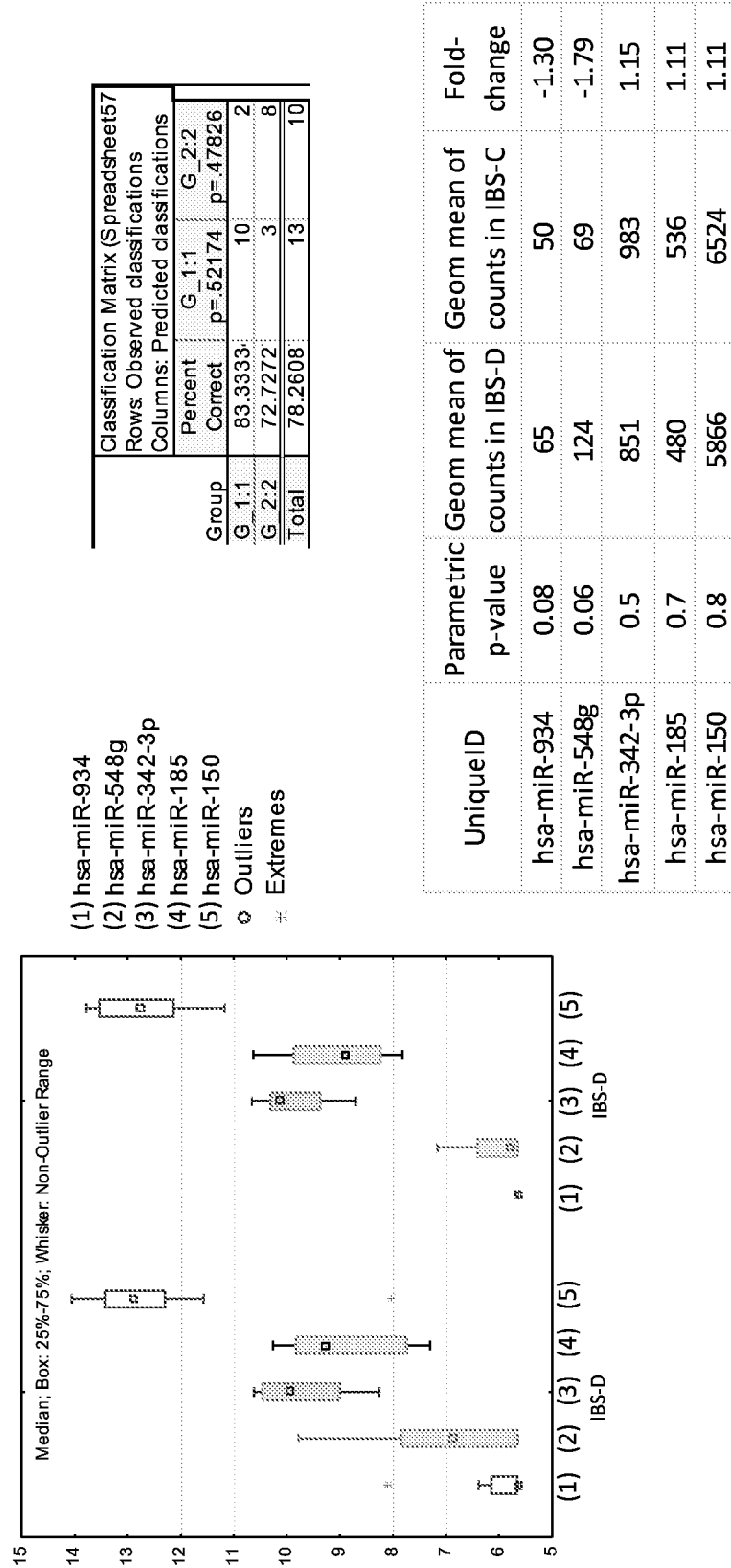

The results show altered expression of miRNAs in in IBS samples compared to control samples from healthy subjects (FIG. 5), in IBS-D samples compared to health control samples (FIG. 6), in IBS-C samples compared to healthy control samples (FIG. 7), and in IBS-D samples compared to IBS-C samples (FIGS. 8 and 9). A classification matrix is shown in each figure, illustrating the percentage of samples that were classified in the correct group based on the miRNA expression patters. The total counts from the nanostring assay, as well as fold change in counts between groups are shown. FIG. 10 illustrates the low inter-assay variability of the nanostring assays presented herein.

Figure 5:
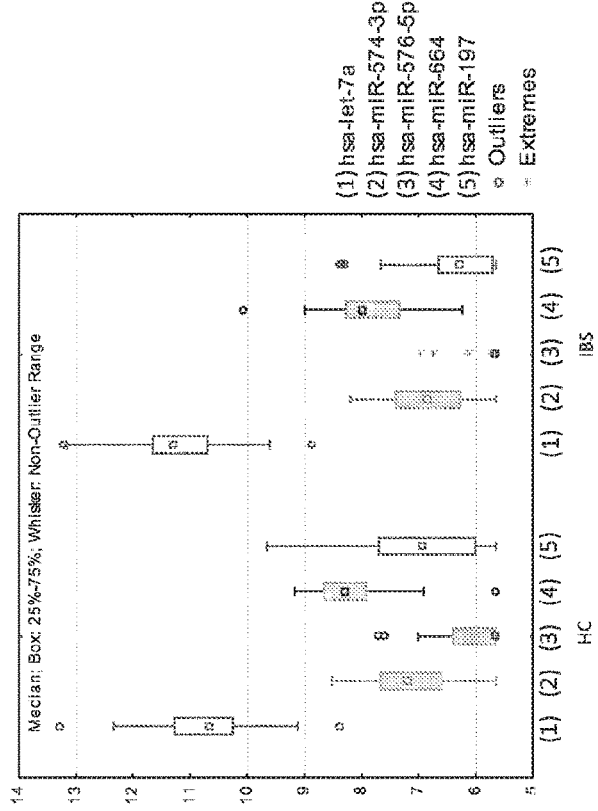

As shown in FIG. 5, when samples from IBS and healthy subjects were compared, an expression profile including an increase in the expression level of hsa-let-7a gene, and a decrease in the expression level of hsa-miR-576-5p, hsa-miR-197, hsa-miR-664, and hsa-miR-574-3p correlated with IBS. The percentage of correct classifications using this signature was approximately 70%.

Figure 6:
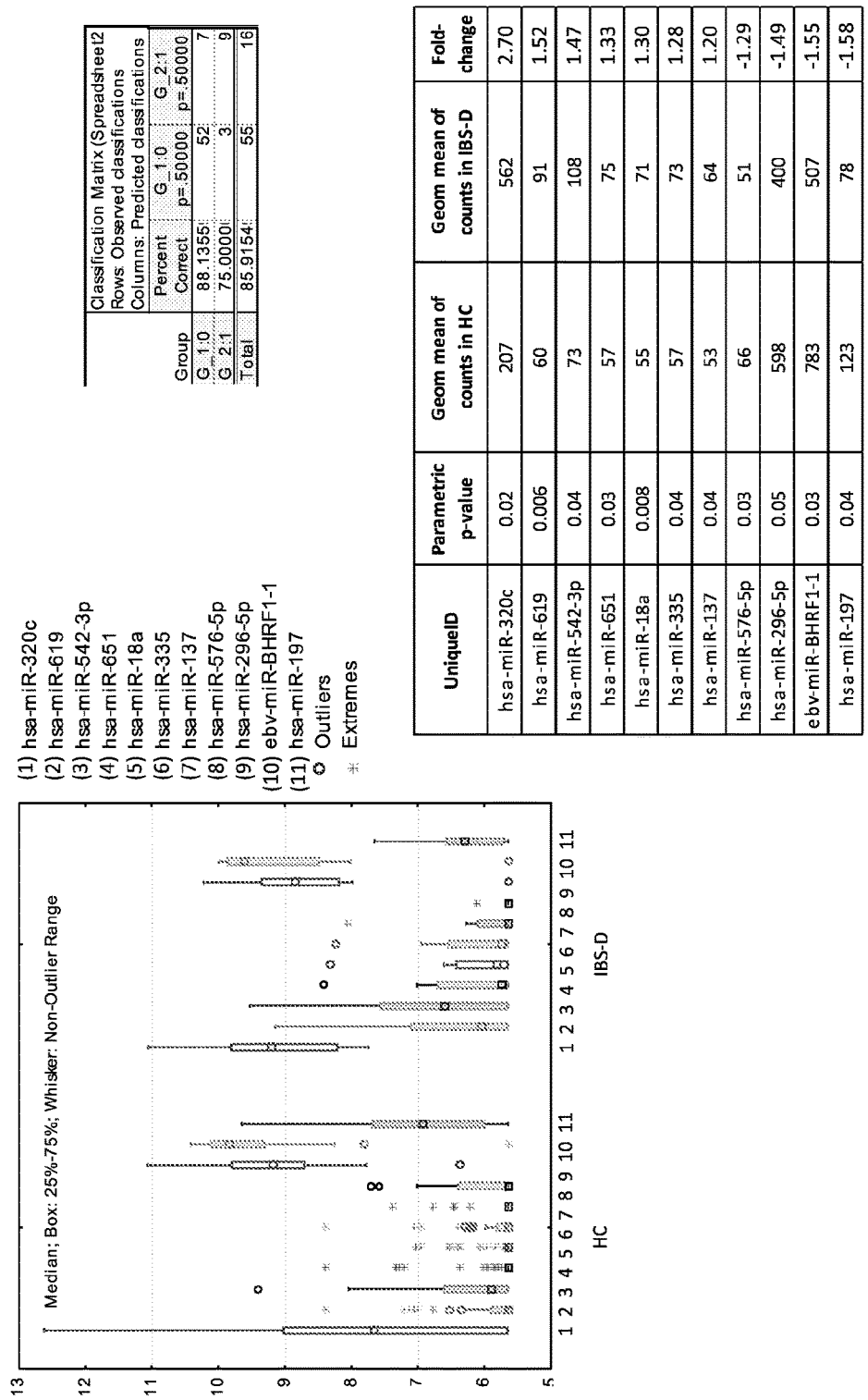

As shown in FIG. 6, when samples from IBS-D and healthy subjects were compared, an expression profile including an increase in the expression level of hsa-miR-619, hsa-miR-542-3p, hsa-miR-651, hsa-miR-18a, hsa-miR-335, hsa-miR-137, and hsa-miR-320c, and a decrease in the expression level of hsa-miR-576-5p, hsa-miR-296-5p, Ebv-miR-BHRF1-1, hsa-miR-197 correlated with IBS-D. The percentage of correct classifications using this signature was approximately 85%.

As shown in FIG. 7, when samples from IBS-C and healthy subjects were compared, an expression profile including an increase in the expression level of hsa-let-7g, hsa-let-7a, hsa-miR-16a, hsa-miR-93, hsa-let-7d, hsa-let-7i, and hsa-miR-98, and a decrease in the expression level of hsa-miR-548g and hsa-miR-423-3p correlated with IBS-C. The percentage of correct classifications using this signature was approximately 92%.

As shown in FIG. 8, when samples from IBS-D and IBS-C were compared, an expression profile including an increase in the expression level of hsa-miR-342-3p, hsa-miR-185, and hsa-miR-150, and a decrease in the expression level of hsa-miR-934 and hsa-miR-548g correlated with IBS-C. The percentage of correct classifications using this signature was approximately 78%.

As shown in FIG. 9, when samples from IBS-D and IBS-C were compared, an expression profile including an increase in the expression level of hsa-let-7g, hsa-let-7d, and hsa-miR-363, and a decrease in the expression level of hsa-miR-335, hsa-miR-379, hsa-miR-619, hsa-miR-1297, and hsa-miR-320c correlated with IBS-C. The percentage of correct classifications using this signature was approximately 78%.

Example 4

Diagnosis of IBS in a Subject

This example describes particular methods that can be used to diagnose or prognose IBS in a subject, such as IBS in a human. However, one skilled in the art will appreciate that similar methods can be used. In some examples, such diagnosis is performed before treating the subject (for example as described in Example 2).

A blood sample is procured from a subject, such as a subject suspected of having IBS. RNA is isolated and purified from the sample using routine methods. Alteration in miR-150 and miR-342-3p are determined by performing real-time PCR (see, Example 1 for detailed procedure). Detection of an at least 2-fold increase in miR-150 and miR-342-3p relative to control values (e.g., expression levels in a blood sample from a healthy subject or a reference value known to be indicative of miR-150 and miR-342-3p expression levels in a blood sample from a healthy subject) is indicative that the subject has IBS.

The results of the test are provided to a user (such as a clinician or other health care worker, laboratory personnel, or patient) in a perceivable output that provides information about the results of the test. The output is a graphical output showing a cut-off value or level that indicates that the subject has or does not have IBS. The output is communicated to the user, for example by providing an output via physical, audible, or electronic means (for example by mail, telephone, facsimile transmission, email, or communication to an electronic medical record). The output is accompanied by guidelines for interpreting the data, for example, numerical or other limits that indicate the presence or absence of metastasis. The guidelines need not specify whether IBS is present or absent, although it may include such a diagnosis. The indicia in the output can, for example, include normal or abnormal ranges or a cutoff, which the recipient of the output may then use to interpret the results, for example, to arrive at a diagnosis, prognosis, or treatment plan. Based upon the results, a therapeutic regimen is or is not recommended.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method of identifying and treating a subject with irritable bowel syndrome (IBS), comprising:
   performing one or more assays that detect an expression level of two or more of miR-150, miR-342-3p, miR-335, miR-151-3p, miR-151-5p, miR-574-3p, and miR-362-5p gene products in a biological sample from the subject;
   comparing the expression level of the gene products to a respective control expression level of the gene products;
   wherein detection of an altered expression level of the two or more of the miR-150, miR-342-3p, miR-335, miR-151-3p, miR-151-5p, miR-574-3p, and miR-362-5p gene products as compared to the respective control identifies the subject as a subject with IBS; and
   treating the subject with the IBS by administering to the subject a therapeutically effective amount of:
   (1) one or more antisense compounds that decrease the expression of the miR-150 and miR342-3p gene products;
   (2) one or more antisense compounds that decrease the expression level of the miR-574-3p, miR-362-5p, and miR-342-3p gene products, and a therapeutically effective amount of one or more agents that increase the level of the miR-335, miR-151-3p, and miR-151-5p gene products in the subject; or
   (3) one or more agents that decrease expression of any of miR-150, miR-342-3p, miR-335, miR-151-3p, miR-151-5p, miR-574-3p, or miR-362-5p that have an altered expression level that is up-regulated in the subject; and one or more agents that increase exspression of any of miR-150, miR-342-3p, miR-335, miR-151-3p, miR-151-5p, miR-574-3p, or miR-362-5p that have an altered expression level that is down-regulated in the subject.

2. The method of claim 1, wherein the one or more assays detect the expression level of the miR-150 and miR-342-3p gene products, and wherein detecting an increased expression level of the miR-150 and miR-342-3p gene products compared to the respective control identifies the subject as a subject with IBS.

3. The method of claim 1, wherein the one or more assays detect the expression level of the miR-342-3p, miR-335, miR-151-3p, miR-151-5p, miR-574-3p, and miR-362-5p gene products, and wherein detecting an increased expression level of the miR-335, miR-151-3p, and miR-151-5p gene products, and a decreased expression level of the miR-574-3p, miR-362-5p, and miR-342-3p gene products, as compared to the respective control identifies the subject as a subject with IBS.

4. The method of claim 1, wherein the control comprises a standard value of the miR-150, miR-342-3p, miR-335, miR-151-3p, miR-151-5p, miR-574-3p, and/or miR-362-5p gene products, respectively, in one or more subjects known not to have IBS.

5. The method of claim 1, further comprising detecting a decrease in the expression level of ebv-miR-BHRF1-1, ebv-miR-BART6-5p, or both ebv-miR-BHRF1-1 and ebv-miR-BART6-5p gene products in the sample from the subject as compared to the control.

6. The method of claim 5, wherein the control comprises a standard value of the ebv-miR-BHRF1-1 or ebv-miR-BART6-5p gene products in one or more subjects known not to have IBS.

7. The method of claim 2, wherein
(a) the decrease is a decrease in expression level of at least about 1.5-fold compared to the control;
(b) the increase is an increase in expression level of at least about 1.5-fold compared to the control; or
(c) a combination of (a) and (b).

8. The method of claim 1, further comprising selecting the subject with IBS for treatment for IBS.

9. The method of claim 8, further comprising administering to the subject a therapeutically effective amount of an agent for the treatment or prevention of IBS.

10. The method of claim 1, wherein:
the method comprises (1) and the antisense compound is an antisense oligonucleotide, siRNA or ribozyme that targets the miR-150 and miR342-3p gene products; or
the method comprises (2) and the one or more antisense compounds comprise antisense oligonucleotides, siRNAs, or ribozymes that targets the miR-574-3p, miR-362-5p, and miR-342-3p gene products, and/or the one or more agents that increase the level of the miR-335, miR-151-3p, and miR-151-5p comprise isolated miR-335, miR-151-3p, and miR-151-5p.

11. A method of,
identifying and treating a subject with irritable bowel syndrome (IBS), comprising:
performing one or more assays that detect an expression level of hsa-let-7a, hsa-miR-576-5p, hsa-miR-197, hsa-miR-664, and hsa-miR-574-3p gene products in a biological sample from the subject;
comparing the expression level of the gene products to a respective control expression level of the gene products;
wherein detection of an increase in the expression level of the hsa-let-7a gene product, and a decrease in the expression level of the hsa-miR-576-5p, hsa-miR-197, hsa-miR-664, and hsa-miR-574-3p gene products, as compared to the respective control identifies the subject as a subject with IBS; and
treating the subject with the IBS by administering to the subject a therapeutically effective amount of:
(1) an antisense compound that decreases the expression level of the hsa-let-7a gene product, and a therapeutically effective amount of one or more agents that increase the level of the hsa-miR-576-5p, hsa-miR-197, hsa-miR-664, and hsa-miR-574-3p gene products in the subject, thereby treating the subject with the IBS; or
(2) one or more agents that decrease expression of any of hsa-let-7a, hsa-miR-576-5p, hsa-miR-197, hsa-miR-664, and hsa-miR-574-3p that have an altered expression level that is upregulated in the subject: and one or more agents that increase expression of any of hsa-let-7a, hsa-miR-576-5p, hsa-miR-197, hsa-miR-664, and hsa-miR-574-3p that have an altered expression level that is down-regulated in the subject.

12. The method of claim 11, wherein
the control is a standard value of the hsa-let-7a, hsa-miR-576-5p, hsa-miR-197, hsa-miR-664, and hsa-miR-574-3p gene products in one or more subjects known not to have IBS.

13. The method of claim 11,
further comprising detecting a decrease in the expression level of the ebv-miR-BHRF1-1, ebv-miR-BART6-5p, or both ebv-miR-BHRF1-1 and ebv-miR-BART6-5p gene products in the sample from the subject as compared to the control.

14. The method of claim 13, wherein
the control is a standard value of the ebv-miR-BHRF1-1 or ebv-miR-BART6-5p gene products in one or more subjects known not to have IBS.

15. The method of claim 1, wherein the sample comprises a blood, tissue, plasma, serum, or stool sample.

16. The method of claim 1, wherein the one or more assays comprise a polymerase chain reaction, a microarray analysis, or a hybridization reaction, a reverse transcriptase polymerase chain reaction (RT-PCR) and/or a nanostring assay.

17. A method of identifying and treating a subject with irritable bowel syndrome with diarrhea (IBS-D), comprising:
performing one or more assays that detect an expression level of hsa-miR-619, hsa-miR-542-3p, hsa-miR-651, hsa-miR-18a, hsa-miR-335, hsa-miR-137, hsa-miR-320c, hsa-miR-576-5p, hsa-miR-296-5p, Ebv-miR-BHRF1-1, and hsa-miR-197 gene products in a biological sample from the subject;
comparing the expression level of the gene products to a respective control expression level of the gene products;
wherein detection of an increase in the expression level of the hsa-miR-619, hsa-miR-542-3p, hsa-miR-651, hsa-miR-18a, hsa-miR-335, hsa-miR-137, and hsa-miR-320c gene products, and a decrease in the expression level of the hsa-miR-576-5p, hsa-miR-296-5p, Ebv-miR-BHRF1-1, hsa-miR-197 gene products, as compared to the respective control identifies the subject as a subject with IBS-D; and
treating the subject with the IBS-D by administering to the subject a therapeutically effective amount of:
(1) one or more antisense compounds that decrease the expression level of the hsa-miR-619, hsa-miR-542-3p, hsa-miR-651, hsa-miR-18a, hsa-miR-335, hsa-miR-137, and hsa-miR-320c gene products, and a therapeutically effective amount of one or more agents that increase the level of hsa-miR-576-5p, hsa-miR-296-5p, Ebv-miR-BHRF1-1, hsa-miR-197 gene products in the subject; or
(2) one or more agents that decrease expression of any of hsa-miR-619, hsa-miR-542-3p, hsa-miR-651, hsa-miR-18a, hsa-miR-335, hsa-miR-137, hsa-miR-320c, hsa-miR-576-5p, hsa-miR-296-5p, Ebv-miR-BHRF1-1, and hsa-miR-197 that have an altered expression level that is up-regulated in the subject; and one or more agents that increase expression of any of hsa-miR-619, hsa-miR-542-3p, hsa-miR-651, hsa-miR-18a, hsa-miR-335, hsa-miR-137, hsa-miR-320c, hsa-miR-576-5p, hsa-miR-296-5p, Ebv-miR-BHRF1-1, and hsa-miR-197 that have an altered expression level that is down-regulated in the subject.

18. The method of claim 17, wherein the control is a standard value of the hsa-miR-619, hsa-miR-542-3p, hsa-miR-651, hsa-miR-18a, hsa-miR-335, hsa-miR-137, hsa-miR-320c, hsa-miR-576-5p, hsa-miR-296-5p, Ebv-miR-BHRF1-1, and hsa-miR-197 gene products in one or more subjects known not to have IBS-D.

19. The method of claim 17, further comprising detecting a decrease in the expression level of the ebv-miR-BART6-5p gene product in the sample from the subject as compared to the control.

20. The method of claim 19, wherein the control is a standard value of the ebv-miR-BART6-5p gene product in one or more subjects known not to have IBS-D.

21. A method of identifying and treating a subject with irritable bowel syndrome with constipation (IBS-C), comprising:
performing one or more assays that detect an expression level of hsa-let-7g, hsa-let-7a, hsa-miR-16a, hsa-miR-93, hsa-let-7d, hsa-let-7i, and hsa-miR-98, hsa-miR-548g and hsa-miR-423-3p gene products in a biological sample from the subject;
comparing the expression level of the gene products to a respective control expression level of the gene products;
wherein detection of an increase in the expression level of the hsa-let-7g, hsa-let-7a, hsa-miR-16a, hsa-miR-93, hsa-let-7d, hsa-let-7i, and hsa-miR-98 gene products, and a decrease in the expression level of the hsa-miR-548g and hsa-miR-423-3p gene products, as compared to the respective control identifies the subject as a subject with IBS-C and
treating the subject with the IBS-C by administering to the subject a therapeutically effective amount of:
(1) one or more antisense compounds that decrease the expression level of hsa-let-7g, hsa-let-7a, hsa-miR-16a, hsa-miR-93, hsa-let-7d, hsa-let-7i, and hsa-miR-98 gene products, and a therapeutically effective amount of one or more agents that increase the level of the hsa-miR-548g and hsa-miR-423-3p gene products in the subject; or
(2) one or more agents that decrease expression of any of hsa-let-7g, hsa-let-7a, hsa-miR-16a, hsa-miR-93, hsa-let-7d, hsa-let-7i, and hsa-miR-98, hsa-miR-548g and hsa-miR-423-3p that have an altered expression level that is up-regulated in the subject; and one or more agents that increase expression of any of hsa-let-7g, hsa-let-7a, hsa-miR-16a, hsa-miR-93, hsa-let-7d, hsa-let-7i, and hsa-miR-98, hsa-miR-548g and hsa-miR-423-3p that have an altered expression level that is down-regulated in the subject.

22. The method of claim 21, wherein the control is a standard value of the hsa-let-7g, hsa-let-7a, hsa-miR-16a, hsa-miR-93, hsa-let-7d, hsa-let-7i, and hsa-miR-98, hsa-miR-548g, and hsa-miR-423-3p gene products in one or more subjects known not to have IBS-C.

23. The method of claim 21, further comprising detecting a decrease in the expression level of ebv-miR-BHRF1-1, ebv-miR-BART6-5p, or both ebv-miR-BHRF1-1 and ebv-miR-BART6-5p gene products in the sample from the subject as compared to the control.

24. The method of claim 23, wherein the control is a standard value of the ebv-miR-BHRF1-1 or ebv-miR-BART6-5p gene products in one or more subjects known not to have IBS-C.

* * * * *

SEQUENCE LISTING

```
<160> NUMBER OF SEQ ID NOS: 39

<210> SEQ ID NO 1
<211> LENGTH: 22
<212> TYPE: RNA
<213> ORGANISM: Epstein Barr virus

<400> SEQUENCE: 1
uaagguuggu ccaauccaua gg                                              22
```

<210> SEQ ID NO 2
<211> LENGTH: 66
<212> TYPE: RNA
<213> ORGANISM: Epstein Barr virus

<400> SEQUENCE: 2
uauuaaccug aucagccccg gaguugccug uuucaucacu aaccccgggc cugaagaggu    60
ugacaa                                                               66

<210> SEQ ID NO 3
<211> LENGTH: 22
<212> TYPE: RNA
<213> ORGANISM: homo sapiens

<400> SEQUENCE: 3
uaaccugauc agccccggag uu                                             22

<210> SEQ ID NO 4
<211> LENGTH: 80
<212> TYPE: RNA
<213> ORGANISM: homo sapiens

<400> SEQUENCE: 4
ugggaugagg uaguagguug uauaguuuua gggucacacc caccacuggg agauaacuau    60
acaaucuacu gucuuuccua                                                80

<210> SEQ ID NO 5
<211> LENGTH: 87
<212> TYPE: RNA
<213> ORGANISM: homo sapiens

<400> SEQUENCE: 5
ccuaggaaga gguaguaggu ugcauaguuu uagggcaggg auuuugccca caaggaggua    60
acuauacgac cugcugccuu ucuuagg                                        87

<210> SEQ ID NO 6
<211> LENGTH: 84
<212> TYPE: RNA
<213> ORGANISM: homo sapiens

<400> SEQUENCE: 6
aggcugaggu aguaguuugu acaguuugag ggucuaugau accacccggu acaggagaua    60
acuguacagg ccacugccuu gcca                                           84

<210> SEQ ID NO 7
<211> LENGTH: 89
<212> TYPE: RNA
<213> ORGANISM: homo sapiens

<400> SEQUENCE: 7
gucagcagug ccuuagcagc acguaaauau uggcguuaag auucuaaaau uaucuccagu    60
auuaacugug cugcugaagu aagguugac                                      89

<210> SEQ ID NO 8
<211> LENGTH: 71
<212> TYPE: RNA
<213> ORGANISM: homo sapiens

<400> SEQUENCE: 8

```
uguucuaagg ugcaucuagu gcagauagug aaguagauua gcaucuacug cccuaagugc    60
uccuucuggc a                                                        71

<210> SEQ ID NO 9
<211> LENGTH: 71
<212> TYPE: RNA
<213> ORGANISM: homo sapiens

<400> SEQUENCE: 9
uguguuaagg ugcaucuagu gcaguuagug aagcagcuua gaaucuacug cccuaaaugc    60
cccuucuggc a                                                        71

<210> SEQ ID NO 10
<211> LENGTH: 80
<212> TYPE: RNA
<213> ORGANISM: homo sapiens

<400> SEQUENCE: 10 cuggggcuc caaagugcug uucgugcagg uagugugauu acccaaccua cugcugagcu     60
agcacuuccc gagcccccgg                                                80

<210> SEQ ID NO 11
<211> LENGTH: 119
<212> TYPE: RNA
<213> ORGANISM: homo sapiens

<400> SEQUENCE: 11
aggauucugc ucaugccagg gugagguagu aaguuguauu guugugggu agggauauua     60 ggccccaauu agaagauaac uauacaacuu acuacuuucc cuggugugug gcauauuca    119

<210> SEQ ID NO 12
<211> LENGTH: 102
<212> TYPE: RNA
<213> ORGANISM: homo sapiens

<400> SEQUENCE: 12
gguccucuga cucucuucgg ugacggguau ucuuggugg auaauacgga uuacguuguu     60
auugcuuaag aauacgcgua gucgaggaga guaccagcgg ca                      102

<210> SEQ ID NO 13
<211> LENGTH: 23
<212> TYPE: RNA
<213> ORGANISM: homo sapiens

<400> SEQUENCE: 13
uguaguguuu ccuacuuuau gga                                            23

<210> SEQ ID NO 14
<211> LENGTH: 84
<212> TYPE: RNA
<213> ORGANISM: homo sapiens

<400> SEQUENCE: 14
cuccccaugg cccugucucc caacccuugu accagugcug ggcucagacc cugguacagg    60 ccuggggac agggaccugg ggac                                            84

<210> SEQ ID NO 15
<211> LENGTH: 21
<212> TYPE: RNA
<213> ORGANISM: homo sapiens
```

<400> SEQUENCE: 15
cuagacugaa gcuccuugag g                                            21

<210> SEQ ID NO 16
<211> LENGTH: 21
<212> TYPE: RNA
<213> ORGANISM: homo sapiens

<400> SEQUENCE: 16
ucgaggagcu cacagucuag u                                            21

<210> SEQ ID NO 17
<211> LENGTH: 82
<212> TYPE: RNA
<213> ORGANISM: homo sapiens

<400> SEQUENCE: 17 aggggggcgag ggauuggaga gaaaggcagu uccugauggu ccccucccca ggggcuggcu   60
uuccucuggu ccuucccucc ca                                           82

<210> SEQ ID NO 18
<211> LENGTH: 75
<212> TYPE: RNA
<213> ORGANISM: homo sapiens

<400> SEQUENCE: 18
ggcugugccg gguagagagg gcagugggag guaagagcuc uucacccuuc accaccuucu   60
ccacccagca uggcc                                                   75

<210> SEQ ID NO 19
<211> LENGTH: 21
<212> TYPE: RNA
<213> ORGANISM: homo sapiens

<400> SEQUENCE: 19 agggccccccc cucaauccug u                                           21

<210> SEQ ID NO 20
<211> LENGTH: 20
<212> TYPE: RNA
<213> ORGANISM: homo sapiens

<400> SEQUENCE: 20
aaaagcuggg uugagagggu                                              20

<210> SEQ ID NO 21
<211> LENGTH: 94
<212> TYPE: RNA
<213> ORGANISM: homo sapiens

<400> SEQUENCE: 21
uguuuugagc gggggucaag agcaauaacg aaaaauguuu gucauaaacc guuuuucauu   60
auugcuccug accuccucuc auuugcuaua uuca                              94

<210> SEQ ID NO 22
<211> LENGTH: 23
<212> TYPE: RNA
<213> ORGANISM: homo sapiens

<400> SEQUENCE: 22

-continued ucucacacag aaaucgcacc cgu                                              23

<210> SEQ ID NO 23
<211> LENGTH: 24
<212> TYPE: RNA
<213> ORGANISM: homo sapiens

<400> SEQUENCE: 23
aauccuugga accaggugu gagu                                              24

<210> SEQ ID NO 24
<211> LENGTH: 75
<212> TYPE: RNA
<213> ORGANISM: homo sapiens

<400> SEQUENCE: 24
uguugucggg uggaucacga ugcaauuuug augaguauca uaggagaaaa auugcacggu       60
auccaucugu aaacc                                                       75

<210> SEQ ID NO 25
<211> LENGTH: 67
<212> TYPE: RNA
<213> ORGANISM: homo sapiens

<400> SEQUENCE: 25
agagauggua dacuauggaa cguaggcguu augauuucug accauguaa cauggccac         60 uaacucu                                                                67

<210> SEQ ID NO 26
<211> LENGTH: 23
<212> TYPE: RNA
<213> ORGANISM: homo sapiens

<400> SEQUENCE: 26
agcucggucu gaggccccuc agu                                              23

<210> SEQ ID NO 27
<211> LENGTH: 22
<212> TYPE: RNA
<213> ORGANISM: homo sapiens

<400> SEQUENCE: 27
ugugacagau ugauaacuga aa                                               22

<210> SEQ ID NO 28
<211> LENGTH: 89
<212> TYPE: RNA
<213> ORGANISM: homo sapiens

<400> SEQUENCE: 28
aguuauuaga uuagugcaaa aguaauugca guuuuugcau uacguucuau ggcaaaacug       60
uaauuacuuu uguaccaaca uaauacuuc                                        89

<210> SEQ ID NO 29
<211> LENGTH: 22
<212> TYPE: RNA
<213> ORGANISM: homo sapiens

<400> SEQUENCE: 29
cacgcucaug cacacaccca ca                                               22

```
<210> SEQ ID NO 30
<211> LENGTH: 22
<212> TYPE: RNA
<213> ORGANISM: homo sapiens

<400> SEQUENCE: 30
auucuaauuu cuccacgucu uu                                              22

<210> SEQ ID NO 31
<211> LENGTH: 99
<212> TYPE: RNA
<213> ORGANISM: homo sapiens

<400> SEQUENCE: 31
cgcccaccuc agccucccaa aaugcuggga uuacaggcau gagccacugc ggucgaccau     60
gaccuggaca uguuugugcc caguacuguc aguuugcag                            99

<210> SEQ ID NO 32
<211> LENGTH: 96
<212> TYPE: RNA
<213> ORGANISM: homo sapiens

<400> SEQUENCE: 32
cagugcuggg gucucaggag gcagcgcucu caggacguca ccaccauggc cugggcucug     60
cuccuccuca ccucccucac ucagggcaca ggugau                               96

<210> SEQ ID NO 33
<211> LENGTH: 97
<212> TYPE: RNA
<213> ORGANISM: homo sapiens

<400> SEQUENCE: 33
aaucuaucac ugcuuuuuag gauaagcuug acuuuuguuc aaauaaaaau gcaaaaggaa     60
aguguauccu aaaaggcaau gacaguuuaa uguguuu                              97

<210> SEQ ID NO 34
<211> LENGTH: 82
<212> TYPE: RNA
<213> ORGANISM: homo sapiens

<400> SEQUENCE: 34
gaacauugaa acuggcuagg gaaaaugauu ggauagaaac uauuauucua uucauuuauc     60
cccagccuac aaaaugaaaa aa                                              82

<210> SEQ ID NO 35
<211> LENGTH: 22
<212> TYPE: RNA
<213> ORGANISM: homo sapiens

<400> SEQUENCE: 35
ugagaccucu ggguucugag cu                                              22

<210> SEQ ID NO 36
<211> LENGTH: 77
<212> TYPE: RNA
<213> ORGANISM: homo sapiens

<400> SEQUENCE: 36
ggaagugccc uacuuggaaa ggcaucaguu gcuuagauua cauguaacua uucccuuucu     60
gaguagagua agucuua                                                    77
```

```
<210> SEQ ID NO 37
<211> LENGTH: 83
<212> TYPE: RNA
<213> ORGANISM: homo sapiens

<400> SEQUENCE: 37
agaaauaagg cuucugucua cuacuggaga cacugguagu auaaaaccca gagucuccag        60
uaauggacgg gagccuuauu ucu                                                83

<210> SEQ ID NO 38
<211> LENGTH: 65
<212> TYPE: RNA
<213> ORGANISM: homo sapiens

<400> SEQUENCE: 38
agaaagaagg aaauugaauu cauuuagaaa agagaauucc aaaugagcuu aauuuccuuu        60
uuucu                                                                   65

<210> SEQ ID NO 39
<211> LENGTH: 77
<212> TYPE: RNA
<213> ORGANISM: homo sapiens

<400> SEQUENCE: 39
uguuuaucuc uaggguugau cuauuagaau uacuuaucug agccaaagua auucaaguaa        60
uucaggugua gugaaac                                                      77
```